US011713465B2

(12) United States Patent
Duncan et al.

(10) Patent No.: US 11,713,465 B2
(45) Date of Patent: Aug. 1, 2023

(54) METHODS FOR TRANSFORMING WHEAT EXPLANTS AND COMPOSITIONS THEREFOR

(71) Applicant: MONSANTO TECHNOLOGY LLC, St. Louis, MO (US)

(72) Inventors: David R. Duncan, St. Charles, MO (US); Sarah Heifner, St. Louis, MO (US); David Kelm, St. Louis, MO (US); Brian J. Martinell, Mt. Horeb, WI (US); Lorena Moeller, St. Louis, MO (US); Anatoly Rivlin, Brooklyn, NY (US); Rebecca Rode, St. Louis, MO (US); Xudong Ye, Madison, WI (US); Ashok Shrawat, Chesterfield, MO (US); Yurong Chen, Chesterfield, MO (US)

(73) Assignee: MONSANTO TECHNOLOGY, LLC, St. Louis, MO (US)

( * ) Notice: Subject to any disclaimer, the term of this patent is extended or adjusted under 35 U.S.C. 154(b) by 0 days.

(21) Appl. No.: 14/550,694

(22) Filed: Nov. 21, 2014

(65) Prior Publication Data
US 2022/0340916 A1 Oct. 27, 2022

Related U.S. Application Data

(60) Provisional application No. 61/907,317, filed on Nov. 21, 2013.

(51) Int. Cl.
C12N 15/00 (2006.01)
C12N 15/82 (2006.01)
(52) U.S. Cl.
CPC ..... *C12N 15/8205* (2013.01); *C12N 15/8209* (2013.01)
(58) Field of Classification Search
CPC .................................. C12N 15/8201
See application file for complete search history.

(56) References Cited

U.S. PATENT DOCUMENTS

| 6,995,016 | B2 | 2/2006 | Eudes et al. | |
|---|---|---|---|---|
| 7,524,522 | B2 | 4/2009 | DeLine et al. | |
| 7,938,345 | B2 | 5/2011 | Teeter, Jr. et al. | |
| 2005/0005321 | A1 | 1/2005 | Martinell et al. | |
| 2008/0124727 | A1 | 5/2008 | Rout et al. | |
| 2008/0280361 | A1* | 11/2008 | Calabotta ............... | A01H 4/003 435/430 |
| 2009/0138985 | A1* | 5/2009 | Martinell et al. ............. | 800/278 |
| 2022/0340925 | A1 | 10/2022 | Chen et al. | |

FOREIGN PATENT DOCUMENTS

| EP | 1521840 B1 | 4/2010 |
|---|---|---|
| WO | WO 2003/0017752 | 3/2003 |
| WO | WO 2004/007736 | 1/2004 |

OTHER PUBLICATIONS

Li et al. 2002. Developmental, tissue culture, and genotypic factors affecting plat regeneration from shoot apical meristems of germinated *Sea mays* L. seedlings. In Vitro cell. Dev. Biology-Plant 38: 285-292.*
Parmar et al. 2012. Plant regeneration from mature embryo of commercial Indian bread wheat (*Triticum aestivum* L.) cultivars. Physiol. Mol. Biol. Plants 18: 177-183.*
The Seed Biology Place: Gerhard Leubner Lab of the University of London (http://www.seedbiology.de/structure.asp).*
Poehlman, J.M. 1987. Breeding field crops, 3rd ed. Van Nostram Reinhold Publisher, p. 39. (Year: 1987).*
Leubner. 2007. Structure and germination of a cereal grain: Triticum aestivum in The seed Biology Place. http://seedbiology.de/structure.asp#structure1. (Year: 2007).*
Chai et al., "Optimum moisture contents of seeds stored at ambient temperatures," *Seed Science Research* 8:23-28, 1998.
Johnston et al., "Mass Isolation of Viable Wheat Embryos," *Nature* 179:160-161, 1957.
Senaratna et al., "Dehydration Injury in Germinating Soybean (*Glycine max* L. Merr.) Seeds," *Plant Physiol.* 72:620-624, 1983.
Vertucci et al., "Theoretical Basis of Protocols for Seed Storage," *Plant Physiol.* 94:1019-1023, 1990.
Raven et al., "The Mature Embryo and Seed," *Biology of Plants.* W. H. Freeman and Company Publishers, 2005. p. 503.
Abdelnour-Esquivel et al., "Cryopreservation of Zygotic Embryos of *Coffea* ssp.," Cryo-Letters 13:297-302, 1992.
Cho et al., "Transformation of recalcitrant barley cultivars through improvement of regenerability and decreased albinism," *Plant Science* 138:229-244, 1998.
Cho et al., "High-frequency transformation of oat via microprojectile bombardment of seed-derived highly regenerative cultures," *Plant Science* 148:9-17, 1999.
Cho et al., "Production of transgenic tall fescue and red fescue plants by particle bombardment of mature seed-derived highly regenerative tissues," *Plant Cell Reports* 19:1084-1089, 2000.
Cho et al., "Transformed $T_0$ orchardgrass (*Dactylis glomerata* L.) plants produced from highly regenerative tissues derived from mature seeds," *Plant Cell Reports* 20:318-324, 2001.
Cho et al., "Stable transformation of rice (*Oryza sativa* L.) via microprojectile bombardment of highly regenerative, green tissues derived from mature seed," *Plant Cell Reports* 22:483-489, 2004.
Ha et al., "Stable Transformation of a Recalcitrant Kentucky Bluegrass (*Poa pratensis* L.) Cultivar Using Mature Seed-Derived Highly Regenerative Tissues," *In Vitro Cell. Dev. Biol.-Plant* 37:6-11, 2001.
Higley et al., "Effects of non-destructive tissue extraction on the viability of corn, soybean, and bean seeds," *Seed Sci. & Technol.* 22:245-252, 1994.

(Continued)

*Primary Examiner* — Karen M Redden
(74) *Attorney, Agent, or Firm* — Dentons US LLP; Paula DeGrandis

(57) ABSTRACT

The present invention provides methods for the transformation of viable explants from wheat seeds to permit production of transgenic wheat plants. The present invention also relates to methods for producing such explants and related embodiments.

16 Claims, 8 Drawing Sheets

(56) References Cited

OTHER PUBLICATIONS

Li et al., "The Level of Expression of Thioredoxin is Linked to Fundamental Properties and Applications of Wheat Seeds," *Molecular Plant* 2:430-441, 2009.

Wilcke et al., "Small Grains Production, Wheat and barley drying," available at http://www.extension.umn.edu/agriculture/small-grains/harvest/wheat-and-barley-drying/, accessed on Dec. 5, 2017.

Zhang et al., "Transformation of recalcitrant maize elite inbreds using in vitro shoot meristematic cultures induced from germinated seedlings," *Plant Cell Reports* 21:263-270, 2002.

Bochardt et al., "DNA Methylation is Involved in Maintenance of an Unusual Expression Pattern of an Introduced Gene," *Plant Physiol.* 99:409-414, 1992.

Hiei et al., "Improved frequency of transformation in rice and maize by treatment of immature embryos with centrifugation and heat prior to infection with *Agrobacterium tumefaciens*," *Plant Cell Tiss. Oman Cult.* 87:233-243, 2006.

Ishida et al. "*Agrobacterium*-mediated transformation of maize," *Nature Protocols* 2(7):1614-1621, 2007.

Karami, "Factors Affecting *Agrobacterium*-Mediated Transformation of Plants," *Transgenic Plant Journal* 2(2):127-137, 2008.

Vertucci et al., "Oxidative Processes in Soybean and Pea Seeds", Plant Physiol. (1987) 84, 1038-1043.

Borisjuk et al., "The oxygen status of the developing seed", New Phytologist (2009) 182, 17-30.

Borisjuk et al., "Tansley Review: The Oxygen Status of the Developing Seed", New Phytologist (2009) 182:17-30; 14 pages.

Miyoshi et al., "Removal of the pericarp and testa seeds of japonica and indica rice (*Oryza sativa*) at various oxygen concentrations has opposite effects on germination", Physiologia Plantarum (1997) 99: 1-6; 7 pages.

Scheiber et al., "Effect of Pericarp Removal, Gibberellic Acid Treatment, and Stratification on Seed Germination of Ableia xgrandiflora", J. Environ. Hort. (Mar. 2003) 21(1):34-37; 5 pages.

Rolletschek et al., "Methodology and Significance of Microsensor-based Oxygen Mapping in Plant Seeds—an Overview", Sensors (2009) 9, 3218-3227; 11 pages.

Talcott et al., "Cold Stratification and Pericarp Removal Improve Seed Germination of Ptelea trifoliata and Ptelea crenulata", HortScience (2020) 55(4):503-506; 4 pages.

USPTO: Response to Non-Final Office Action regarding U.S. Appl. No. 13/873,092, filed Jan. 30, 2023.

U.S. Appl. No. 13/873,092, filed Apr. 29, 2013, Chen et al.

Al-Abed et al., "Split-seed: a new tool for maize researchers," *Planta* 223:1355-1360, 2006.

Gordon-Kamm et al., "Transformation of maize cells and regeneration of fertile transgenic plants," *Plant Cell* 2:603-618, 1990.

Gould et al., "Transformation of *Zea mays* L. using *Agrobacterium tumefaciens* and the shoot apex," *Journal of Plant Physiology* 95:426-434, 1991.

Horn et al., "Use of HI II-Elite inbreds in Agrobacterium-based transformation of maize," *In Vitro Cellular & Developmental Biology—Plant* 42:359-366, 2006.

Huang et al., "High frequency plant regeneration through callus initiation from mature embryos of maize (*Zea mays* L.)," *Plant Cell Reports* 22:793-800, 2004.

Ishida et al., "High efficiency transformation of maize (*Zea mays* L.) mediated by *Agrobacterium tumefaciens*," *Nature Biotechnology* 14:745-750, 1996.

Li et al., "Developmental, tissue culture and genotypic factors affecting plant regeneration from shoot apical meristems of germinating *Zea mays* L. seedlings," *In Vitro Cellular & Developmental Biology—Plant* 38:285-292, 2002.

Sairam et al., "Shoot meristem: an ideal explants for *Zea mays* L. transformation," *Genome* 46:323-329, 2003.

Sidorov et al., "Agrobacterium mediated transformation of seedling-derived maize callus," *Plant Cell Reports* 25:320-328, 2006.

Songstad et al., "Production of transgenic maize plants and progeny by bombardment of Hi-II immature embryos," *In Vitro Cellular & Developmental Biology—Plant* 32:179-183, 1996.

Sticklen et al., "Shoot apical meristem: A sustainable explants for genetic transformation of cereal crops," *In Vitro Cellular & Developmental Biology—Plant* 41:187-200, 2005.

Wang et al., "Callus induction and plant regeneration from maize mature embryos," *Plant Cell Reports* 6:360-362, 1987.

Zhang et al., "Transformation of recalcitrant maize inbreds using in vitro shoot meristematic cultures induced from germinated seedlings," *Plant Cell Reports* 21:263-270, 2002.

Zhong et al., "In vitro morphogenesis of corn (*Zea mays* L.). I. Differentiation of multiple shoot clumps and somatic embryos from shoot tip," *Planta* 187:483-489, 1992.

Zhong et al., "The competence of maize shoot meristems for integrative transformation and inherited expression of transgenes," *Plant Physiology* 110:1097-1107, 1996.

\* cited by examiner

METHODS FOR TRANSFORMING WHEAT EXPLANTS AND COMPOSITIONS THEREFOR

REFERENCE TO RELATED APPLICATIONS

This application claims the benefit of U.S. provisional Application No. 61/907,317 filed Nov. 21, 2013, which is incorporated herein by reference in its entirety.

BACKGROUND OF THE INVENTION

1. Field of the Invention

The invention relates to novel methods for wheat seed explant transformation.

2. Description of Related Art

Wheat (*Triticum* spp.) is an important crop and a primary food source in many areas of the world. Biotechnological techniques have been used to significantly improve wheat and other crop species in a number of agronomic and food quality traits. Development of transgenic crops, in particular, requires plant explant materials capable of being genetically transformed and regenerated into a transgenic plant capable of passing a transgene to progeny.

SUMMARY OF THE INVENTION

In one aspect, the invention provides a method of producing a transgenic wheat plant comprising transforming a wheat dry seed derived explant competent for genetic transformation, wherein the explant comprises an intact embryo including the scutellum and embryonic axis obtained from a dry wheat seed; and wherein endosperm and pericarp have been substantially removed from the explant. In specific embodiments, the explant is defined as in a state of metabolic stasis at the time of said transforming. In another embodiment, the metabolic stasis is characterized by an oxygen consumption rate of from about 0.05 to about 0.5 nMoles $O_2$/ml/min/explant at transformation. In one embodiment, the transformation comprises *Agrobacterium*-mediated transformation.

In certain embodiments, a method of the invention comprises culturing the explant for from about 0 hours to about 112 days prior to said transforming. In another embodiment, transforming the explant is carried out within about 2 hours of first contacting the explant with an aqueous solution. In such aspects, it is contemplated that transformation is carried out under conditions where the explant is capable of taking up transforming (heterologous) DNA, which may then be integrated into the genome of the plant cell. In this methodology, the cell and/or transforming DNA may or may not be treated to facilitate the uptake and/or integration of the DNA in the chromosome. Transforming the explant may be carried out without generating a callus from the explant prior to transformation. The explant may be decontaminated during the process. Culturing the explant to produce multiple buds may be carried out following said transforming. The explant may also be hydrated for about 0.5-2 hours. In still another embodiment, the explant is stored for from about 1 hour to about 2 years prior to transformation, including storage for about 0, 2, 4, 6, 8, 10, 12, 14, 16, 18, 20, 22, or 24 hours, 1, 2, 3, 4, 5, 6, 7, 14, 21, or 28 days, 1, 2, 3, 4, 5, 6, 7, 8, 9, 10, 11, or 12 months, or 1, or up to 2 years. In specific embodiments, a plurality of wheat seed explants are transformed. In certain embodiments, the explant comprises an internal moisture content at which the explant does not germinate without addition of hydration. In further embodiments, the explant is stored at an internal moisture content of from about 5% to about 12% prior to rehydrating the explant during or prior to said transforming. In still further embodiments, transforming comprises co-culturing the explant with *Agrobacterium* sp. for not more than about 7 days.

In another aspect, the invention provides a method of producing a transgenic progeny wheat plant comprising obtaining a transgenic wheat plant prepared by a method of the invention and obtaining transgenic progeny of the transgenic wheat plant that comprise the heterologous DNA.

In yet another aspect, the invention provides for methods of transforming a purified population of wheat dry seed derived explants competent for genetic transformation and capable of regeneration into a plant, wherein the explants are comprised of complete intact embryos including the scutellum and entire embryonic axis; wherein remaining portions of the wheat seed have been substantially removed from the explants. In one embodiment such an explant is defined as a viable explant. Therefore, the seed explants may be defined as mostly devoid of tissues such as endosperm and pericarp. In certain embodiments, the explants comprise an internal moisture content that will not result in germination, and/or the explant is produced from a seed with an internal moisture content at which the seed will not germinate without the application of exogenous moisture. In further embodiments, such an internal moisture content may be from about 3% to about 25% w/w, including about 3, 5, 7, 9, 11, 13, 15, 17, 19, 21, 23, or 25%, and including between about 3% to about 8%, between about 5% to about 10%, between about 6% to about 12%, between about 8% to about 15%, and between about 10% to about 20%. In certain embodiments, the production of explants is automated; and in further embodiments, at least a first explant is produced by grinding off the surface of a wheat seed.

In still another aspect, the invention provides a purified population of wheat dry seed derived explants competent for genetic transformation and use thereof as described, but further wherein the explants are produced from immature wheat seeds. In particular embodiments, such explants may be produced by obtaining an immature wheat seed and dehydrating the seed followed by production of an explant as described herein, such as in the case of an explant comprised of an intact embryo including the scutellum and embryonic axis and mostly devoid of other tissues such as endosperm and pericarp. In specific embodiments, the dehydrating or drying may result in a seed and/or explant comprising an internal moisture content as described herein.

In still yet another aspect, the invention provides a method of producing a wheat dry seed derived explant viable for regeneration into a plant and use thereof, comprising substantially removing the portions of a mature wheat seed other than the complete intact embryos including the scutellum and entire embryonic axis. The wheat dry seed derived explants are therefore mostly devoid of other tissues such as endosperm and pericarp. Such explants are competent for genetic transformation. In another embodiment of the invention, tissue is removed from the seed manually. In one example, manual removal of seed portions is carried out by grinding. The explant may also be prepared in an automated process. In further embodiments, the explant may be produced from a seed having, and/or may comprise, an internal moisture content from about 3% to about 25%, including about 3, 5, 7, 9, 11, 13, 15, 17, 19, 21, 23, or 25%, and including between about 3% and about 8%, between about 5% to about 10%, between about 6% to about 12%, between about 8% to about 15%, and between about 10% to about 20%. In still further embodiments, the explant is defined as comprising a size between about 0.75 mm$^2$ to about 2 mm$^2$, including from about 0.75 mm$^2$ to 1.75 mm$^2$, from about 0.75 mm$^2$ to 1.25 mm$^2$, from about 1.0 mm$^2$ to about 2 mm$^2$, from about 1.25 mm$^2$ to 2.0 mm$^2$, and from about 1.0 mm$^2$ to about 1.75 mm$^2$, including all exact values included within each of these ranges.

The foregoing and other aspects of the invention will become more apparent from the following detailed description.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

DETAILED DESCRIPTION OF THE INVENTION

Figure 1:
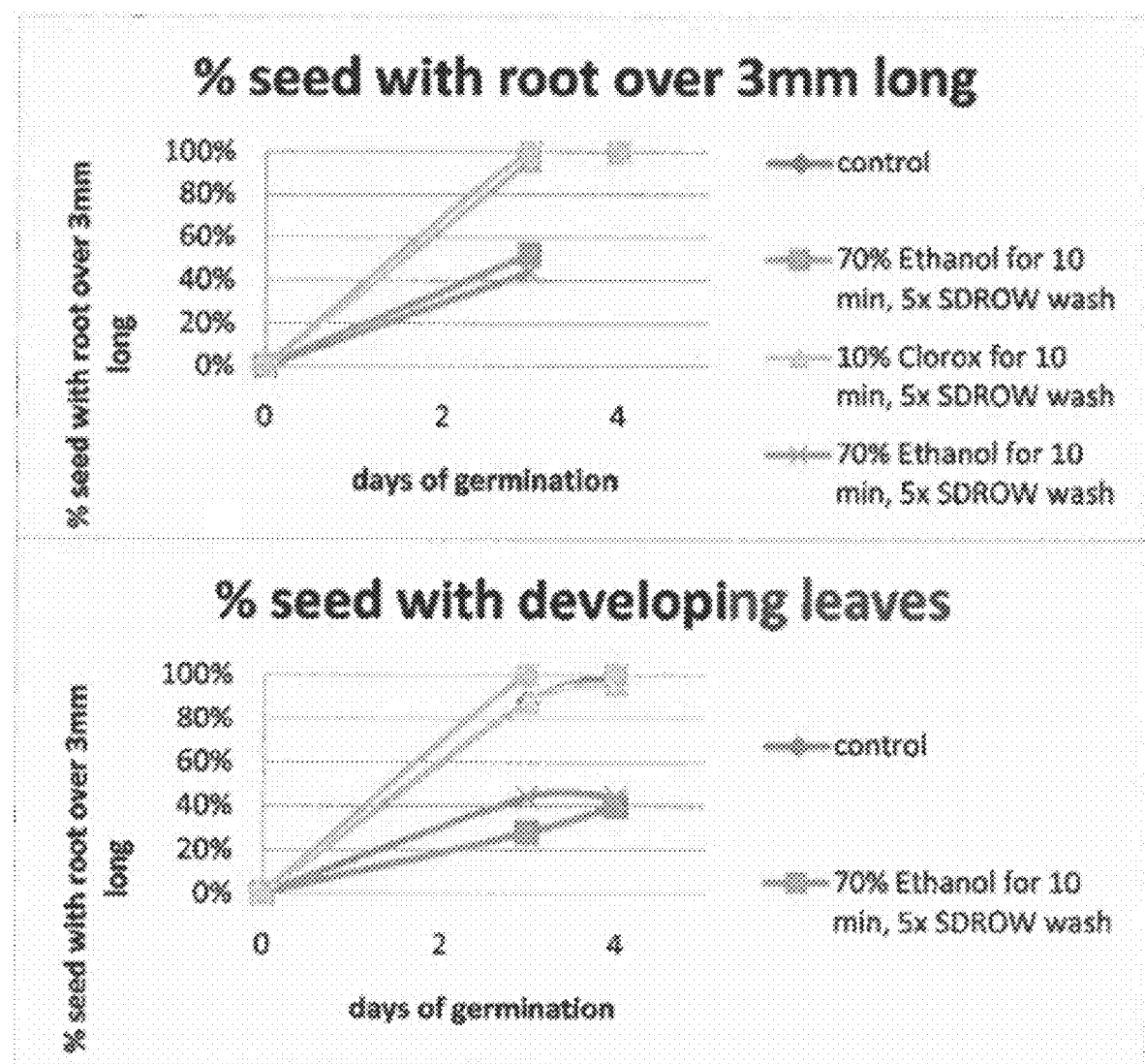
FIG. 1: Shows effect of various sanitization treatments on wheat seed germination.

The following is a detailed description of the invention provided to aid those skilled in the art in practicing the present invention. Those of ordinary skill in the art may make modifications and variations in the embodiments described herein without departing from the spirit or scope of the present invention.

The current invention provides methods for production of transgenic wheat plants by transformation of wheat dry seed derived explants (WDSDEs). Such explants may be produced by removal of seed parts from a mature wheat seed to obtain an explant comprising the completely intact viable embryos including the scutellum and entire embryonic axis, as described herein.

In accordance with the invention, a plurality of WDSDEs can be produced to provide a stable supply from field-grown mature seeds for production of transgenic wheat plants. This system eliminates the requirement of large greenhouse spaces for explant production and reduces variations associated with the growth of donor plants in the greenhouse and downstream transgenic production. Use of WDSDEs also avoids the inflexibility in scheduling of immature embryo-based transformation systems, in which initiation of studies is dependent on successful pollination of donor ear and may require approximately a 2-month waiting period for donor plants to grow.

The WDSDEs explant transformation system described herein allows handling of large amounts of explants in a single study, and is storable, shippable, and readily amenable to automation. Other variations in wheat transformation may further be avoided by use of WDSDEs, such as physiological conditions of immature embryos, the size and stage of immature embryos. Further, environmental conditions that influence the physiological status of immature embryos, such as source, seasons, and pest infestation, contribute greatly to the variation in transformation efficiency.

The development of such a system avoids the need for use of immature embryos and the associated problems therewith. The implementation of the system vastly reduces risks during the production of transformed plants having valuable new phenotypes, which often requires production of hundreds if not thousands of different transgenic plants to identify just a single commercial transformation event. Program-wide efforts to produce transgenic plants with new traits valuable to farmers can require production of many thousands of transgenic plants in a consistent, quick, and cost-effective manner. The current invention thus advantageously provides large numbers of explants in a steady supply for production of transgenic plants. In specific embodiments of the invention, such explants may be produced and stored prior to transformation. Explant preparation can therefore occur at off-peak times and days, and explants stored for later use, enhancing the efficiency of the overall transformation process. The nature of the explants and their production makes this process much more labor efficient and well suited for high volume, high throughput transformation needs. Manipulation of the moisture content of the seed may also be carried out to adjust seed shattering characteristics and subsequent seed and explant vigor and process yield.

Provided by the invention are methods for transformation of such wheat seed derived explants (WDSDEs). The methods involve, in one embodiment, direct inoculation of wheat WDSDEs with *Agrobacterium* prior to tissue culture, selecting WDSDEs on multiple shoot induction medium, and regenerating transgenic plants on hormone-free selection media. In accordance with the invention, centrifugation or other force may be used at one or more steps to obtain transformed explants. For example, centrifugation may find use during inoculation of plant cells with *Agrobacterium* to enhance transformation efficiency.

The transformation of WDSDEs explants is capable of being coupled with use of a multiple bud pathway for efficient generation of transgenic plants and can be used with various desired selection systems. Selectable markers that may be used include, but are in no way limited to, cp4, aadA, and NPT II. The ability to use such a system to obtain stable integration of transgenes into the wheat genome and germline transmission of transgenes to the next generation is described and confirmed herein.

The invention further provides in specific embodiments methods and compositions for preparing, selecting and using explants, as well as the explants produced thereby. In certain embodiments, explants according to the invention may be produced manually or in an automated process. For example, seed tissues may be removed from a seed by cutting, grinding, abrasion, or any other similar process. Automated methods for removal of unnecessary seed parts may also be carried out. Fluid, for example, can be used to move explants and separate desirable explants from debris during mechanized handling of seeds, including compressed air, other gases, and liquids. Dry excision of plant embryos to yield transformable explant tissue may be performed, for example, followed by immediate use in transformation methods. Alternatively, dry excised explants may be subsequently stored, with or without treatment prior to storage such as dehydration, for later transformation or other use. Explant preparation and/or storage may thus comprise drying explant and/or seed tissue to obtain a desired hydration level, depending upon the initial moisture content of the seed and/or explant prior to or at the time of excision.

In one embodiment, an explant prepared or used in accordance with the invention may be defined as having an internal moisture of about 3-30%, including about 3, 4, 5, 6, 7, 8, 9, 10, 11, 12, 13, 14, 15, 16, 17, 18, 19, 20, 21, 22, 23, 24, 25, 26, 27, 28, 29, and 30% internal moisture, and specifically including all ranges derivable between any two such values, and/or may be defined as produced from a mature seed having any such moisture content. In specific aspects, the moisture may be measured while an explant is in storage prior to rehydration or prior to or as part of a transformation process, as well as at the time of such a process.

Explants produced in accordance with the invention may be transformed at various times after removal from the mature wheat seed and isolation therefrom. In one embodiment, explants are relatively "young" in that they have been removed from seeds for less than a day, for example, from about 1 to 24 hours, such as about 2, 3, 5, 7, 10, 12, 15, 20, or 23 hours prior to use. In other embodiments, explants may be stored for longer periods, including days, weeks, months or even years, depending upon storage conditions used to maintain ultimate explant viability. In other embodiments, explants may be rehydrated prior to transformation, for example, about 1, 2, 4, 6, 12, or 24 hours prior to transformation. Those of skill in the art in particular will understand that storage and/or rehydration times may be optimized such that the quality and/or yield of transformants as well as the efficiency of the transformation process is maximized. This can be carried out for any particular transformation protocol, for example, such as *Agrobacterium*-mediated transformation, microprojectile bombardment transformation, as well as other transformation procedures.

Prior to explant generation and use, seeds may be subjected to an optional culling step intended to remove seeds with a high degree of bacterial or fungal contamination or seeds that may for any reason be unlikely to produce viable embryonic tissue for use with the present invention. Culling may be carried out, for example, based on parameters such as the size, color, or density of the seed or other physical characteristics that in other contexts would be unobjectionable, and may be adjusted empirically by variation of the excision, sterilization, and storage parameters and by measurement of ultimate yields of viable tissue and of regeneration and transformation efficiencies. Examples of culling methods may include the use of an automatic scale after size sorting. An optical sorter suitable for this purpose is the Sortex Seed Sorter or the Satake ScanMaster™ II (Satake USA Inc., Houston, Tex.). Other culling techniques may also be employed including culling by moisture content.

In certain embodiments of the invention, explants may be washed prior to use in a fluid, which can be a gas or liquid. An example of use of a gas includes flushing dry explants in sterile air while de-ionizing explants to remove static. Further, specifically charged plates and UV germicidal lamps can be used to remove undesirable particles such as contaminants and microscopic dust. Dry explants may also be subjected to a hydration to increase internal moisture content prior to being transformed with a heterologous nucleic acid. Transformation is alternatively carried out prior to priming or germination.

The invention may in particular aspects involve sterilization of explants prior to excision and/or post-excision. Sterilization can include contacting seed or explant material with various fluids (i.e., liquid or gaseous) that serve to reduce or eliminate the presence of viable bacterial or fungal contaminants that could otherwise interfere with seed or embryo viability and later plant tissue culture. Sterilization by application of liquid may also hydrate or partially hydrate the plant tissues, and serve the purpose of priming seeds or embryos. Methods for sterilization include, but are not limited to, the use of chlorine gas, ozone, solutions of bleach or alcohol, ultraviolet light, temperatures of −20° C. or lower, and exposure to a temperature higher than 40° C.

Removal of seed parts to produce an explant in accordance with the invention may be performed in an automated manner, as well as manually and including by an individual using a variety of mechanical techniques in order to isolate the explant. Seeds may be modified using tools such as forceps or by hand, such as with a grinding tool providing an abrasive force. A seed may be initially fractured followed by manual completion of the explant. Manual fracturing of seed may be accomplished, for example, by striking the seed with a hard object, or by using a press, such as a standard arbor press (e.g., Dayton 4Z328A or Dayton 4Z329D; Dayton Tool Company, Dayton, Ohio). Some seeds may be damaged, such as to remove some or all unnecessary portions not to be included in the explant. Selection of the explants having the desired structure can be carried out. As needed, further manual or automated modification may be carried out to obtain the desired explant.

In some embodiments, a dry explant may be first primed, for example, by imbibition of a liquid such as water or a sterilization liquid, and later used for transformation and regeneration. In other embodiments, the seed or the explant may be primed by raising the internal seed moisture content to greater than 30%, holding the seed or the explant at a time point, and then re-initiating imbibition at a later time point. In an alternative embodiment, the seed or the explant may be primed by raising the internal moisture content to greater than 30%, storing the seed or the explant for a predetermined period, drying the seed or the explant to the internal moisture content of below 20%, and then re-initiating imbibition.

A collection of modified seed material may be screened for suitable explants. For example, a candidate explant may be automatically imaged for analysis of pre-determined quality, such as to test for viability, chemical and biological properties, and suitability in the transformation or regeneration process. Desired explant material may be sorted, for example, by manual sieving, such as a series of geological separation sieves, such that unwanted large and small debris are separated from the desired explant by size exclusion. This could be carried out, for instance with wheat material, using U.S. Standard sieves (listed from top to bottom): #16

(1.18 mm opening), and #26 (~0.6 mm opening), and then a collection pan on the bottom. Large debris is collected on the #16 sieve, while desired embryo explant material is retained and collected on the #20 sieve. Unwanted fine particles passed through to the collection pan. The explant yield collected on the #20 sieve may be further purified by placing this yield into a vertical airflow separation column (e.g., a MACS-104 machine Seed Tech Systems, LLC., multiple air chamber system, Wilton, Calif. or an OREGON SEED BLOWER; Hoffman Manufacturing, Jefferson, Oreg.) in which air is passed through the material, blowing lighter unwanted material upward where it is trapped for removal. Modification of the column with various static reduction means would allow for dust removal from embryo surfaces and reduce bio-contamination and remove any unnecessary plant cell and tissue.

Mechanized sieving and airflow separation may also be utilized. For instance, bulk yield from a GP-140 grinder (Modern Process Equipment; Chicago, Ill.) machine that utilizes vibration and gravitational pull to sieve and separate the unwanted seed material from the desired explants. As an example, the Clipper Office Tester or an Eclipse 324 Clipper (Clipper Separation Technologies; A.T. Ferrell Company, Bluffton, Ind.) may be utilized. This machine has two slots for separation screens to be inserted, whereby seed material is separated according to size. In addition, this machine utilizes a fan that duplicates the function of the previously mentioned vertical airflow separation device, thus giving a final purified yield of explants in a single step.

Various particle separation devices have been successfully used to isolate useful WDSDEs, such as: an Eclipse 324 seiver, an Indented Cylinder Separator (Westrup Model LA-T fitted with 2.0 mm indent cylinder, Westrup A/S Slagelse, Denmark) and a MACS-104 machine (Seed Tech Systems, LLC., multiple air chamber system, Wilton, Calif.). This does not represent a complete list of devices that can successfully isolate and recover dry transformable explants from seeds. Using these devices in sequence may be desirable for efficiency and purity of product.

Candidate explant material may be harvested, screened as needed, and selected or subjected to further manual or automated modification. In specific embodiments, one of skill in the art may store explants prepared according to the invention prior to subsequent use. Methods and parameters for drying, storing, and germinating seed are known in the art (e.g., Senaratna et al., 1983, *Pl. Physiol.* 72:620-624, 1983; Vertucci and Roos, 1990, *Pl. Physiol.* 90:1019-1023, 1990; Chai et al., 1998, *Seed Science Research* 8 (Supplement 1):23-28, 1998). Any such conditions may be used as desired, including at temperatures, for example, of from about −80° C. to about 60° C. Temperatures of about −20° C. to room temperature in particular have been found to function well, but the invention is in no way limited to these temperatures.

Various methods have been developed for transferring genes into explant tissue including high velocity microprojection, microinjection, electroporation, direct DNA uptake, and bacterially-mediated transformation. Bacteria known to mediate plant cell transformation include a number of species of the Rhizobiaceae, including, but not limited to, *Agrobacterium* sp., *Sinorhizobium* sp., *Mesorhizobium* sp., and *Bradyrhizobium* sp. (e.g., Broothaerts et al., 2005, *Nature*, 433:629-633, 2005; U.S. Patent Application Publication 2007/0271627). Targets for such transformation have often been undifferentiated callus tissues, although differentiated tissue also has been used for transient and stable plant transformation. As is well known in the art, other methods for plant transformation may be utilized, for instance as described by Miki et al., (1993, "Procedures for Introducing Foreign DNA into Plants," in *Methods in Plant Molecular Biology and Biotechnology*, Glick B. R. and Thompson, J. E. Eds., CRC Press, Inc., Boca Raton, pages 67-88), including use of microprojectile bombardment (e.g., U.S. Pat. No. 5,914,451; McCabe et al., 1991, *Bio/Technology* 6:923-926, 1988; U.S. Pat. Nos. 5,015,580; 5,550,318; 5,538,880).

The transformed explant or tissues grown therefrom may be cultured in the presence of a selection agent such as the herbicide glyphosate. The result of this step is the termination or at least growth retardation of most of the cells into which the foreign genetic construction has not been delivered and the simultaneous induction of the formation of shoots, which arise from a small cluster of cells including a transformed cell. The transformed tissue can also be cultivated in the presence of other selection agents alone or in combination, including, but not limited to herbicides such as glufosinate, acetolactate synthase inhibitors, protoporphyrinogen oxidase inhibitors, and hydroxyphenyl-pyruvate-dioxygenase inhibitors, or antibiotic inhibitors such as neomycin, kanamycin, paromomycin, G418, aminoglycosides, streptomycin, hygromycin B, bleomycin, phleomycin, sulfonamides, streptothricin, chloramphenicol, methotrexate, 2-deoxyglucose, betaine aldehyde, S-aminoethyl L-cysteine, 4-methyltryptophan, D-xylose, D-mannose, benzyladenine-N-3-glucuronidase. Examples of various selectable markers and genes providing resistance against them are disclosed in Miki and McHugh, 2004. In one embodiment of the invention a coding region for the selectable marker aminoglycoside adenyltransferase (aadA) conferring resistance to or streptomycin is used (e.g., U.S. Pat. No. 5,217,902; or Sandvang, 1999, *Antimicrob. Agents Chemotherapy* 43:3036-3038).

Unmodified and modified protein molecules and their corresponding nucleic acid molecules providing herbicide tolerances to one or more of the following herbicides are well known in the art. They are exemplified below and are incorporated herein by reference:

a) sequences encoding tolerance to glyphosate include 5-enolpyruvylshikimate-3-phosphate synthases (EPSPS; U.S. Pat. No. 5,627,061, U.S. Pat. RE39,247, U.S. Pat. Nos. 6,040,497, 5,094,945, WO04074443, and WO04009761), glyphosate oxidoreductase (GOX; U.S. Pat. No. 5,463,175), glypho state decarboxylase (WO05003362 and U.S. Patent Application 20040177399), and glyphosate-N-acetyl transferase (GAT; U.S. Patent publication 20030083480) conferring tolerance to glyphosate;

b) phosphinothricin acetyltransferase (bar) conferring tolerance to phosphinothricin or glufosinate (U.S. Pat. Nos. 5,646,024; 5,561,236; EP 275,957; U.S. Pat. Nos. 5,276,268; 5,637,489; 5,273,894);

c) 2,2-dichloropropionic acid dehalogenase conferring tolerance to 2,2-dichloropropionic acid (Dalapon) (WO9927116);

d) acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. Nos. 6,225,105; 5,767,366; 4,761,373; 5,633,437; 6,613,963; 5,013,659; 5,141,870; 5,378,824; 5,605,011);

e) haloarylnitrilase (Bxn) for conferring tolerance to bromoxynil (WO8704181A1; U.S. Pat. No. 4,810,648; WO8900193A);

f) modified acetyl-coenzyme A carboxylase for conferring tolerance to cyclohexanedione (sethoxydim) and aryloxyphenoxypropionate (haloxyfop) (U.S. Pat. No. 6,414,222);

g) dihydropteroate synthase (sulI) for conferring tolerance to sulfonamide herbicides (U.S. Pat. Nos. 5,597,717; 5,633,444; 5,719,046);

h) 32 kD photosystem II polypeptide (psbA) for conferring tolerance to triazine herbicides (Hirschberg et al., 1983);

i) anthranilate synthase for conferring tolerance to 5-methyltryptophan (U.S. Pat. No. 4,581,847);

j) dihydrodipicolinic acid synthase (dapA) for conferring to tolerance to aminoethyl cysteine (WO8911789);

k) phytoene desaturase (crtI) for conferring tolerance to pyridazinone herbicides such as norflurazon (JP06343473);

l) hydroxy-phenyl pyruvate dioxygenase for conferring tolerance to cyclopropylisoxazole herbicides such as isoxaflutole (WO 9638567; U.S. Pat. No. 6,268,549);

m) modified protoporphyrinogen oxidase I (protox) for conferring tolerance to protoporphyrinogen oxidase inhibitors (U.S. Pat. No. 5,939,602); and n) aryloxyalkanoate dioxygenase (AAD-1) for conferring tolerance to an herbicide containing an aryloxyalkanoate moiety (WO05107437). Examples of such herbicides include phenoxy auxins (such as 2,4-D and dichlorprop), pyridyloxy auxins (such as fluroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac).

A variety of tissue culture media are known that, when supplemented appropriately, support plant tissue growth and development, including formation of mature plants from excised meristems or embryos. These tissue culture media can either be purchased as a commercial preparation or custom prepared and modified by those of skill in the art. Examples of such media include, but are not limited to those described by Murashige and Skoog, (1962, *Physiol Plant* 15:473-497); Chu et al., (1975, *Sci. Sinica* 18:659-668); Linsmaier and Skoog, (1965, *Physiol. Plant.* 18: 100-127, 1965); Uchimiya and Murashige, (1962); Gamborg et al., (1968, *Exp Cell Res.* 50:151-8); Duncan et al., (1985, *Planta* 165:322-332); McCown and Lloyd, (1981, *Combined Proc. Int. Plant Propagator's Soc.*, 30: 421-427); Nitsch and Nitsch, (1969, *Science* 163:85-87); and Schenk and Hildebrandt, (1972, *Can. J. Bot.* 50:199-204), or derivations of these media supplemented accordingly. Those of skill in the art are aware that media and media supplements such as nutrients and growth regulators for use in transformation and regeneration are usually optimized for the particular target crop or variety of interest. Reagents are commercially available and can be purchased from a number of suppliers (see, for example Sigma Chemical Co., St. Louis, Mo., and Phytotechnology Laboratories, Shawnee Mission, Kans.).

The following definitions will aid in the understanding of the description of the invention.

"Callus" refers to a dedifferentiated proliferating mass of cells or tissue.

"Explant" refers to a plant part that is capable of being transformed and subsequently regenerated into a transgenic plant.

"Mature wheat seed" refers to a wheat seed that has reached full development, normally accompanied by reduction in internal moisture content.

"Tissue culture media" refers to liquid, semi-solid, or solid media used to support plant growth and development in a non-soil environment. Suitable plant tissue culture media is known to one of skill in the art, as discussed in detail subsequently. The media components can be obtained from suppliers other than those identified herein and can be optimized for use by those of skill in the art according to their requirements.

"Nucleic acid" refers to deoxyribonucleic acid (DNA) or ribonucleic acid (RNA).

"Phenotype" refers to a trait exhibited by an organism resulting from the interaction of genotype and environment.

"Recombinant nucleic acid vector" or "vector" refers to any agent such as a plasmid, bacterial artificial chromosome, cosmid, virus, autonomously replicating sequence, phage, or linear or circular single- or double-stranded DNA or RNA nucleotide segment, derived from any source, capable of genomic integration or autonomous replication, typically comprising a nucleic acid molecule in which one or more nucleic acid sequences have been linked in a functionally operative manner. Such recombinant nucleic acid vectors or constructs may be capable of introducing a 5' regulatory sequence or promoter region and a DNA sequence for a selected gene product into a cell in such a manner that the DNA sequence is transcribed into a functional mRNA, which is subsequently translated into a polypeptide or protein.

"Regeneration" refers to the process of growing a plant from a plant cell.

"Regeneration medium" refers to a plant tissue culture medium formulated for regeneration of a transgenic plant and which may contain a selection agent.

"Regenerable callus" refers to callus from which whole plants can be produced.

"Selectable marker" or "screenable marker" refers to a nucleic acid sequence whose expression confers a phenotype facilitating identification of cells containing the nucleic acid sequence.

"Selection" refers to contacting an inoculated explant with a selection medium for obtaining a transformed cell, tissue, or plant.

"Selection medium" refers to a plant tissue culture medium containing a selection agent.

"Substantially removed" in the context of a seed or seed part refers to the removal of most or all of a defined portion in order to yield a transformation-competent explant as described herein.

"Transgenic" refers to organisms into which an exogenous nucleic acid sequence has been integrated.

"Chimeric" refers to a plant, tissue, explant, or the like, which is composed of two genetically different types of tissue as a result of genetic transformation.

"Transformable explant" refers to any part of a plant that is receptive to transformation.

EXAMPLES

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Example 1

Wheat Dry Excision Protocol

Seed Surface Sanitization:

Wheat seed from four source seed bags (approximately 200 lbs.) were evenly divided into 16 perforated metal trays (15" square by 2.5" deep; perforated holes are approximately 1/16" in diameter). Full trays were loaded into a drainable bulk tank (300 L capacity or similar) in a manner which allows them to be completely submerged by liquid (eight layers with two trays on each layer is standard practice). A perforated plastic divider or similar may be placed between layers of seed trays to allow liquid to easily flow through the seed contents, while ensuring that seed is retained in each tray.

A sanitization solution was prepared in a dispensable container with enough volume to sufficiently submerge all layers of seed within the bulk tank. The sanitization solution was prepared by mixing two parts household bleach (6.15% sodium hypochlorite) with eight parts sterile reverse osmosis water (SROW) and adding 0.01 ml of Tween 20 per each liter of final volume. The recipe was 192 liters SROW+48 liters household bleach+2.4 ml Tween 20. The prepared sanitization solution was drained to a bulk tank containing seeds and filled until all seeds have been submerged. The filling process should conclude in less than 10 minutes.

Seeds were submerged for a period of about 10 minutes. After 10 minutes had elapsed, the liquid was drained, generally in less than 10 minutes. After all sanitization solution had been drained, the seeds were rinsed 3 times with fresh SROW. The process was conducted by filling up the bulk tank with SROW to a level that completely covers all seeds. Once seeds had been covered, the liquid was drained. Filling and draining the tank with SROW was performed 3 times (i.e., 3 rinses). After completion of the final rinse, the seeds/trays were transferred to the Bryair Drier.

Seed Drying:

Seed trays were transferred to the dehumidifying BRY-AIR® Drier (model #VFB-3-E-DXA) and slid into one of 16 tray holders within the drying chamber. The chamber doors were closed and sealed after all trays had been inserted. The drier process air temperature was set to 38° C. and the percent relative humidity (RH) was set at 2%. After approximately 48 hours of drying, the seed trays were removed from the drier and emptied into a bulk vessel. The seeds were gently mixed with a paddle mixer or similar device in a manner to evenly distribute drier and wetter seeds within the population.

Once mixing was complete, the seeds were redistributed into the seed trays and placed back in the drier for an additional 16-24 hours. Seeds were removed from the drier after an additional 16-24 hours of dry time post mixing and sealed in Mylar® bags until excision procedure was to be performed. Final average internal moisture of seed as measured with Farmex grain moisture analyzer (serial #: 005047) was typically 7.2% (+/−1%).

Excision:

Excision was performed by passing seeds through a modified GRAINMAN® Rice Sheller/Dehuller (model #64-115-60-WEC). The sheller was modified by removing the standard synthetic rubber roll and replacing it with a custom made, 8" diameter, stainless steel, knurled wheel. The knurled wheel turns in opposition to the standard stainless steel flailing wheel to provide the shearing action that removes the WDSDE from the corresponding seed material. The flailing wheel was rotated 18 times for every one rotation of the stainless steel wheel (18:1 ratio).

The rear height adjusting set screw on the GRAINMAN® Rice Sheller/Dehuller was adjusted so there was approximately a 15.2 mm gap between the screw anchor guide and the down position resting bar. This full down position was maintained by securing S-hook spring. A vacuum line (~2.5 inches) was attached to the material outflow of the Dehuller and adjusted so the suction velocity as measured with a velometer at the center face of the hose was approximately 750 fpm. This line assists in dust removal of the excised material outflow.

Seed was fed via pneumatic in-line conveyor into the Dehuller at rate of approximately 115 pounds per hour. The compressed air pressure used to achieve conveyance was adjusted to use the minimum possible pressure. Post-excised seeds pass via gravity from the Dehuller into the Eclipse 324 Clipper Cleaner for screening and air separation.

The Eclipse 324 was configured with a top screen of US 18×18 stainless steel woven wire mesh and a bottom screen made of US 35×35 stainless steel woven wire mesh. Under each screen was a ball tray containing three rubber balls in each slot to aid in reduction of screen blinding during processing. The sliding metal air inlet blower baffles were positioned all the way down, and the blower variable frequency drive (VFD) was set to 50%. Large seed material that was retained by the 18×18 wire mesh was collected and retained for an additional pass through the Dehuller. Material that passes through the 18×18 screen was not lifted out through the air stream and was retained by the 35×35 screen as the WDSDE fraction for further processing.

After the first pass was completed, the over 18×18 fraction was re-excised and sieved for a second time in a similar fashion as previously done. All equipment settings with the exception of the Dehuller gap remained the same for this second pass. The Dehuller gap was set to 14.5 mm for this excision pass of material. Processing time for the second pass was between 1.5-2 hours. The WDSDE fraction from this second pass was retained and combined with the WDSDE fraction from the first pass for further separation.

WDSDE Separation:

Subsequent WDSDE separation/purification was performed using the Westrup LA-LS screen cleaner. The screen cleaner was configured with a US 18×18 stainless steel (SS) woven wire mesh scalp screen, a US 22×22 SS woven wire mesh middle screen and a US 35×35 SS woven wire mesh bottom screen. Ball trays were positioned under the middle and bottom trays that contained 4 black rubber balls in each tray location and that aid in screen blinding reduction. The various air settings and material feed speeds were as follows: Fan speed=1; Sieve Boat Speed=2.75; Feed Speed=2.75; Feed Gate=—3/16" up from feed trough; Top Blast Gate=0.25; Bottom Blast Gate=6; Side/End Blast Gate=2.5; Magnehelic indicates ~2 Pascal's.

WDSDE material to be separated was loaded into hopper and processed with these settings for a total run time between 2.5-3 hours. All sized fractions were retained with the exception of the lightest aspirated material (i.e., Bin #5). Retained material was hand sieved using a US 20×20 SS wire mesh screen and US 30×30 SS wire mesh screen. All material retained by these two screens makes up the final WDSDE collection. The final WDSDE collection was scored to determine the number of WDSDEs per gram of dry material and sealed in MYLAR® packets in pre-determined quantities.

Example 2

Wheat Seed Sanitation

Figure 2:
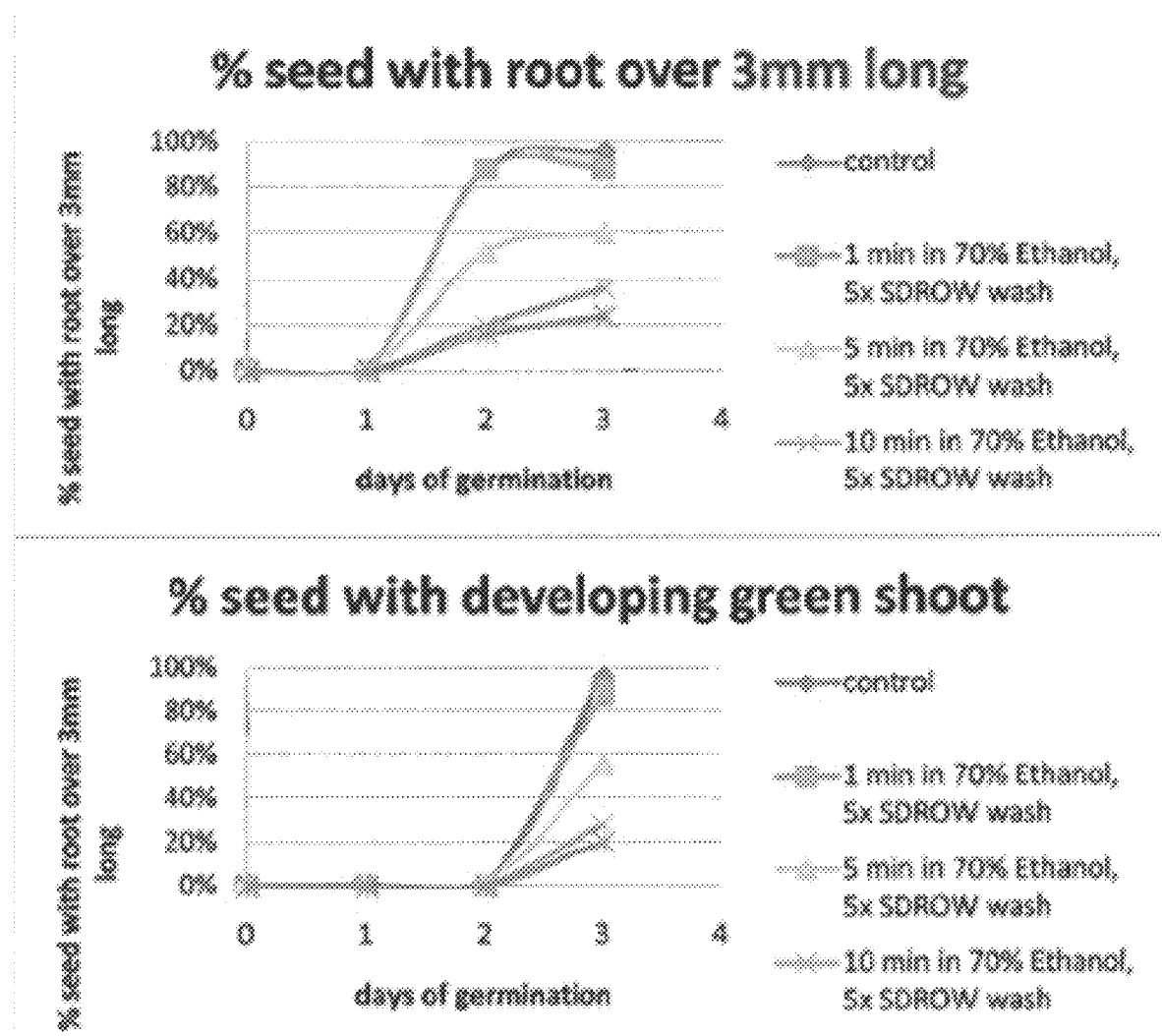
FIG. 2: Shows time-dependent effect of ethanol on wheat seed germination.

It was recognized that seed sanitization was important in consistent production of usable explants for tissue culture work. Traditionally, treatments with 70% ethanol and/or various concentrations of CLOROX® bleach were used to surface-sanitize seed prior to tissue culture work. This approach has been initially tried with wheat seed. To test whether ethanol/CLOROX® bleach treatment may have had a negative effect on explant viability, a more detailed study was conducted. As shown in FIG. 1, treatments involving ethanol reduced germination of intact seeds as measured by root and shoot development on media. More detailed tests showed a time-dependent effect of 70% ethanol exposure on intact seed germination on media (FIG. 2).

To ensure that the effect was not intact-seed specific, explants were excised from the seeds treated in various ways and multiple quality metrics were tested. In this study, ethanol was used cold (~0° C.). 10% Clorox® bleach by itself or in combination with 70% ethanol produced the cleanest WDSDEs. EtOH, $H_2O_2$, and chlorine gas were less efficient. Importantly, here the viability of WDSDEs produced from Clorox® bleach and/or ethanol-treated seed was acceptable. This may be partially due to the use of cold ethanol, or, more likely, the previously-detected negative effect was mostly limited to the intact seed germination. Transformability of the explants derived from this study was to be tested.

Example 3

*Agrobacterium* Preparation for Wheat Transformation: "Short Prep"

A frozen glycerol stock was maintained on dry ice at all times throughout the protocol. A sterile loop was used to obtain a small amount of the frozen glycerol stock and for ABI strains, the *Agrobacterium* was streaked onto an LB plate (Lynx ID #1282) containing spectinomycin, streptomycin, chloramphenicol and kanamycin, sealed with parafilm, and incubated in the dark at 28° C. for three days. The streaked plate(s) was moved to 23° C., dark, for one additional day of culture.

The following inoculation medium was prepared:

| 1/10 CM4C | (Recipe Number 3091) liquid | 200 mls |
|---|---|---|
| Acetosyringone | (1.0M stock) | 40 μl |

A 10 μl sterile yellow loop was used to scoop *Agrobacterium* off of the streaked plate. Two loopfuls of *Agrobacterium* were transferred into 2.5 ml of the inoculation medium+acetosyringone in a 50 ml sterile orange capped centrifuge tube. Vortexing was used to suspend well. The $OD_{660}$ was checked by making a $1/20^{th}$ dilution (50 μl of *Agrobacterium* suspension into 950 μl of inoculation medium) and the OD was measured at 660 nm in a spectrophotometer, using inoculation medium as the blank. The OD was adjusted to 1.0 using inoculation medium. If a different final OD was needed (e.g., an OD of 0.50 was used in certain embodiments), the sample was diluted accordingly.

Example 4

*Agrobacterium* Preparation for AB32

Glycerol stock was taken out of −80° C. freezer, thawed and mixed by vortexing. 0.5 ml glycerol stock was added to 100 ml of LB broth medium (Sigma L7658) with 50 mg/L Spectinomycin and 30 mg/L Gentamycin) in a sterile flask and grown overnight on a shaker at 170 rpms, 27-28° C. in the dark. Approximately 16 hours later (i.e., the following morning), *Agrobacterium* growth phase was determined using a spectrophotometer. A 1:20 dilution of the *Agrobacterium* culture was prepared using LB medium (50 μl *Agrobacterium*+950 μl LB) in a cuvette. 1000 μl LB medium was used as a blank. Generally, the diluted $OD_{660}$ was between 0.020 and 0.080. If the $OD_{660}$ was below 0.020, cultures were further incubated at 28° C. until enough growth occurred. The overnight-grown 100 ml *Agrobacterium* inoculum was divided into two 50 ml centrifuge tubes. The tubes were centrifuged at 3500 rpm for 20 minutes at 20° C. The supernatant was discarded, and each *Agrobacterium* pellet was re-suspended in 5 ml of inoculation medium (Recipe Number 3091). The two tubes were combined and mixed (total 10 ml). The $OD_{660}$ of the suspension was determined and adjusted to a final OD660 of 0.5. A 1:20 dilution (50 μl *Agrobacterium* suspension and 950 μl inoculation medium) was made for a OD660 reading, and the final OD660 was then adjusted to 0.5 by adding inoculation medium.

Example 5

WDSDEs Sterilization, Purification, and Transformation

An entire MYLAR® bag containing 10,000 WDSDEs was poured into a sterile 1-liter bottle. 500 mL of 70% ethanol was added and slowly agitated by inverting and rolling the bottle or by placing it on a shaker for 4-5 minutes.

All WDSDEs were transferred into sterile sieve/collection beakers. 1 liter sterile water was used to complete the transfer. The inner sieve was moved to a fresh sterile beaker for floatation. 2 liters of sterile water was added to the sieve/collection beakers, and the inner sieve was lifted to induce WDSDEs floatation. A vacuum collector was used to remove floating WDSDEs. The inner sieve may be lifted completely out of the sterile water several times in order to collect all WDSDEs. Additional sterile water was added as needed. When more than 50% of the floating material was debris, collection was stopped, and the procedure was continued with the next step. Only WDSDEs were collected. As debris can be a source of contamination, it was avoided.

After collection of WDSDEs was complete, the vacuum was turned off, and the outer bin of the collector was loosened. The gloved hands were sprayed well with ethanol. A bucket was opened, and the inner bucket containing the collected WDSDEs was removed carefully. The inner bucket was placed on a sterile plate lid or an equivalent. WDSDEs were then distributed evenly into two 50 ml centrifuge tubes for inoculation.

WDSDEs inoculation: *Agrobacterium* solution was added to the WDSDEs in 50 ml centrifuge tubes and filled up to a volume of between 40-45 ml. Tubes were centrifuged at 1400 g (calculated based on rotor diameter) for 30 minutes at 4° C. *Agrobacterium* and WDSDEs were resuspended by inverting/shaking the tubes. WDSDEs were allowed to settle to the bottom of the tubes, and the majority of *Agrobacterium* were decanted out of the tubes. Then, the WDSDEs were dispensed into a 100×25 mm plate. *Agrobacterium* containing solution was removed by manual pipetting or vacuum removal.

Co-culture: Plates containing Ahlstrom 1 filter paper and 1.25 ml of co-culture medium (Recipe Number 3091) were prepared. WDSDEs were distributed into approximately 30 plates using 1/16th tsp scoop and spread into a single layer using a sterile spoonula. Plates were incubated in an open box (no lid) at 23° C. and 65-70% RH in the dark for 3-4 days.

Delay: The filter paper was peeled from co-culture plates containing the WDSDEs and placed directly onto the solid delay medium (Recipe Number 3996); cultured for 2 weeks at 25° C. and 16-hrs light cycle, full light.

Selection: Contaminated plates were discarded and recorded. Selection plates were prepared by placing 2 felts and 1 filter paper with a punched hole. 17 ml of selection medium (Recipe Number 3997) was added. Using a sterile spoonula, the WDSDEs were distributed onto the selection plates. Each delay plate was split into 5 selection plates. Plates were incubated at 25° C. and a 16-hour photoperiod under full-light intensity (50-220 µmoles/m$^2$ sec for 1 week (+/−2 days). Then, 5 ml of medium was overlayed, and the plates were cultured for an additional week (+/−2 days).

Regeneration: Plates were observed, and any contaminated plates were removed and recorded. Selection medium was aspirated using a vacuum trap. 20 ml of regeneration medium (Recipe Number 3995) was added to each plate, and the plate was incubated at 25° C. and 16-hours photoperiod under full light intensity for 1 week (+/−2 days). 5 mL regeneration medium (3995) was overlayed, and the plates were cultured for an additional week (+/−2 days). Excess medium was aspirated from the corner of the plate by tipping the plate to the side and placing the aspiration tip at the edge of the plate. 10 ml of regeneration medium (3995) was added, and the plates were cultured for an additional week (+/−2 days). 5 ml of regeneration medium (3995) was overlayed, and the plates were cultured for an additional week (+/−2 days). Shoots were pulled to rooting medium (Recipe Number 3903). 10 mL of regeneration medium was overlayed (3995), and the plates were culture for an additional week (+/−2 days). Shoots were pulled to 3903 rooting medium. Any final shoots were pulled to 3903, and the remaining liquid plates were discarded.

Rooting and Potting: Emerging shoots were placed onto solid medium plates containing rooting medium (3903). One explant was placed per plate. All associated tissues/shoots were removed from the liquid plate to avoid harvesting clones. Shoots can be harvested at 8 and 10 weeks after culture initiation. Final shoots were harvested, and liquid plates were discarded after 11 weeks in culture. Shoots were placed in ¼" peat potting plugs (International Horticulture Technologies, LLC) at 10 and 12 weeks post inoculation.

Example 6

Seed Crushing

One of the first steps in one example of a method of wheat dry seed derived explant production is crushing of the seed. Several different machines have been used for this purpose in an effort to find the optimal mechanism.

Grinding Mill:

A test run of wheat seed through a Grinding Mill set tighter for smaller wheat seed was conducted. This was followed by crude enrichment using an Oregon Blower and a stack of standard sieves. A fraction that was recovered contained abundant wheat embryos. Viability of these explants was tested.

Rice Dehuller:

It was tested whether wheat excision can be done using this equipment. It was found that multiple passes of wheat seed through the rice dehuller resulted in sufficient seed crushing and explant release. WDSDEs were recovered using manual sieving. Initial studies have shown that appreciable yields of wheat WDSDEs can be obtained when wheat grain was passed through the dehuller multiple times. Seed moisture content was a significant factor in improving explant yield. A key advantage of this method was the reduction of process dust, as the wheat seed remained substantially whole while the embryo was abraded from the seed. This also made embryo recovery more efficient.

Example 7

Process Development

A study using the rice dehuller was performed to determine the maximum and minimum roller gap spacing (as measured by the distance between the "square roll support" and the "steel roll support lifting handle") for process optimization, and a range of 12.95 mm-14.50 mm was established. Furthermore, a study was performed to determine the number of passes of seed through the dehuller that would be tested for optimization based on wt. % purity and % yield obtained. The explants were recovered using a US #18 hand sieve. Data collected demonstrated actual yields between 40-50% and a purity range of 6.7 to 9.2% with four dehuller passes, or a yield of 20 to 30% and purity range of 7.0 to 11.0% with two dehuller runs.

Figure 3:
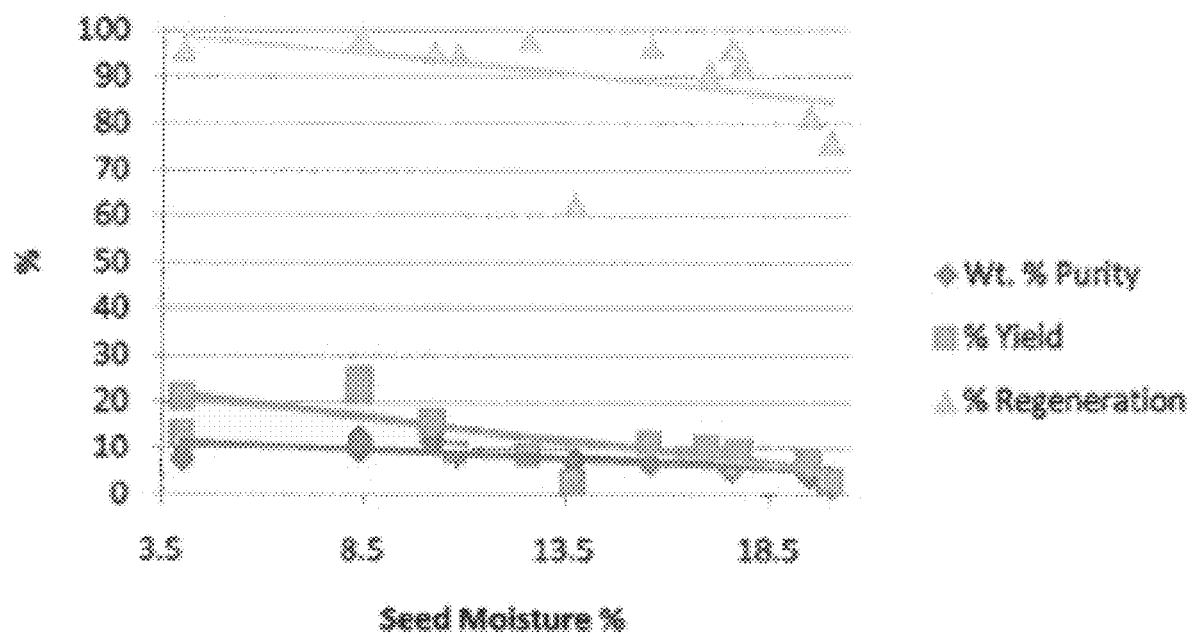
FIG. 3: Shows the effect of internal seed moisture on purity, yield, and regeneration of product.

In addition, a study was performed to optimize the wt. % purity, % yield, and % regeneration of the product obtained by performing two passes of 200-250 g wheat seed samples through the rice dehuller. The process variables tested include the gap spacing of the rollers for each pass through the dehuller and the internal moisture of the wheat seed. The moisture was varied by drying the wheat in a BRY-AIR® Dryer at variable times using standard process conditions of 38° C. and 4.0% relative humidity. FIG. 3 shows the effect of moisture on yield, purity, and regeneration for moisture levels between 4.0-20.0% (measure with the FarmEX Moisture reader). These results were consistent with trends observed in other dehulling studies.

Furthermore, the effect of the dehuller gap spacing between the rollers for each pass through the process was examined to determine any relationship they had with the product purity, yield, and regeneration. During this study, a cyclone attached to the dehuller was used at a constant air flow to remove any light particles from the dehuller product stream. Explants were recovered from this process by use of a screen cleaner (Office Clipper Cleaner) with #18 and #30 screen sizes.

It was found that a higher regeneration percent can be achieved if the first pass gap is larger; however, the second pass gap size had a smaller effect over the range examined. The gap spacing for the first pass had minimal effect on the overall yield, while the data for the second pass suggested that a smaller spacing increased explants yield. Individual results for this study demonstrated that this process achieved 11.2 wt % purity and 21 wt % yield, which was consistent with the other studies performed. The data collected for this study was fitted to optimization curves to determine the parameters needed to obtain a product with an 11.0 wt % purity, 20.6% yield, and a 97% regeneration. The optimization numbers were obtained for an internal seed moisture content of 7.1%, a dehuller gap of 14.13 mm for pass one, and 13.20 mm for pass two. These results were constant with trends observed in the data. Additional purification steps and optimizations can also be performed to increase product purity. A smaller screen cleaner screen size has been shown to increase purity in the wheat excision grinding process. Tests with product from the dehuller demonstrated that use of the Oregon blower can increase purity.

Example 8

Wheat WDSDEs Purification: Floatation Enrichment and Color Sorting

The product of wheat dry excision using the techniques described above usually contained 100-500 wheat WDSDEs per gram. To further enrich WDSDEs, floatation enrichment was used. This resulted in significant enrichment of the WDSDEs. Enriched WDSDEs could be regenerated on media or re-dried to retain viability.

To provide a more prominent difference between wheat WDSDEs and debris particles, iodine staining was tested. Brief staining resulted in strongly differential staining with debris readily staining while WDSDEs remaining largely unstained. Staining pattern was mostly maintained when material was re-dried.

Example 9

Wheat WDSDEs Mechanically Excised from Mature Dry Seed are Viable and Transformable WDSDEs, produced using a grinding mill and precision grinder were recovered by sieving/Oregon blower, and their viability was tested. Briefly, WDSDEs were placed on non-selective media and allowed to regenerate plantlets in Percival set for 28° C., 16 hours of light for about two weeks. Thus, regenerated plantlets were handed off to the green house and grown there. Plants developed normally and set seeds.

To demonstrate that wheat WDSDEs are an effective starting material for transformation, it was important to show that these explants can be infected by *Agrobacterium*. Several attempts were made to transform mechanically excised wheat explants using *Agrobacterium* AB32 and carrying a construct comprising a screenable marker encoding GUS. Inoculated wheat explants grew and showed good transient GUS activity. Importantly, stable expression of GUS in plantlets growing on selection was detected as well.

The range of some variables in the wheat WDSDEs transformation protocol was also tested. In some cases, as with liquid culture, e.g., co-culture time and maltose concentration in the co-culture medium played a significant role in increasing the efficiency of the system.

Figure 4:
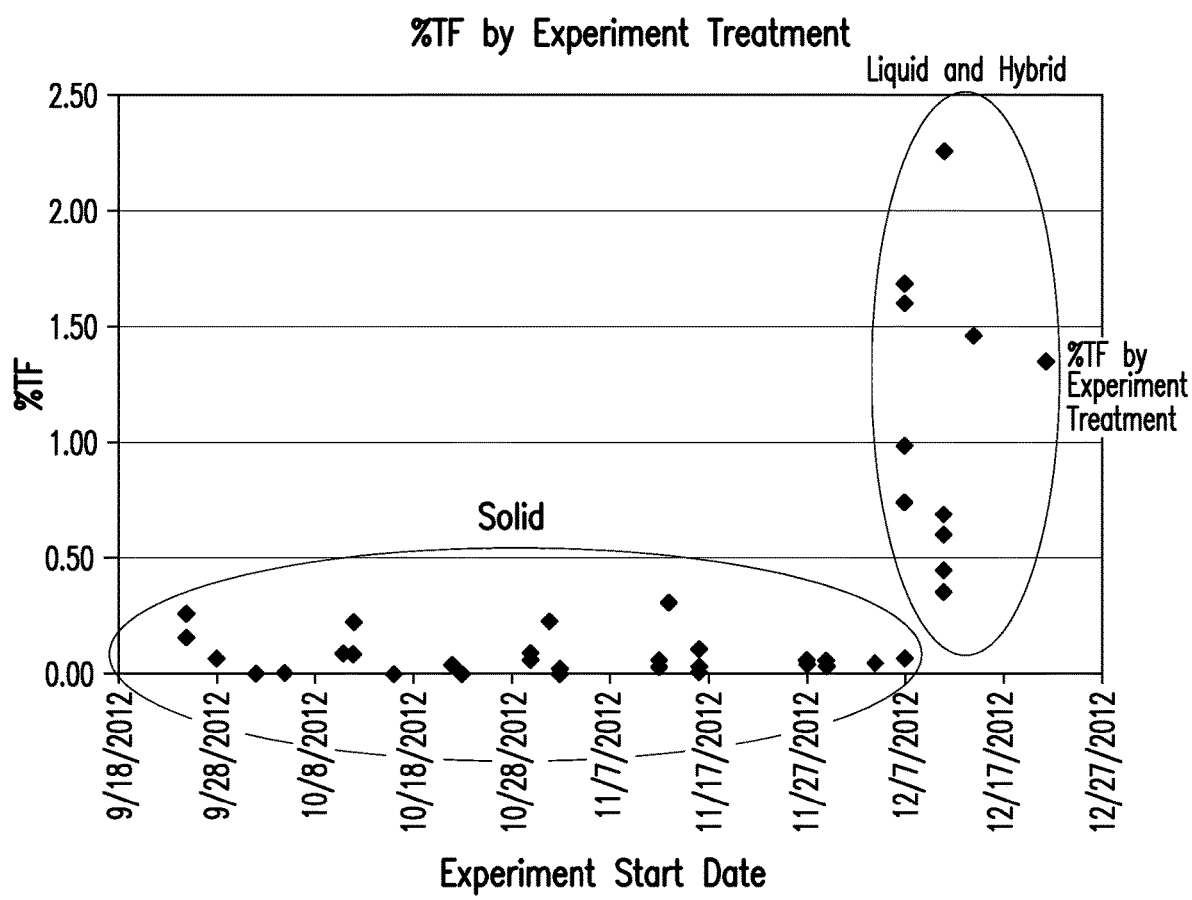
FIG. 4: Shows studies in which the standard protocol using MS-based medium was used in all studies. The results demonstrate the dramatic effect of liquid culture on event production. The tissue support for the liquid culture consisted of two pieces of 100% acrylic felt covered by a single piece of filter paper.

For example, FIG. 4 shows the percentages of transformation frequencies achieved depending on culture method. A standard protocol was used in these experiments, and the effect of liquid culture on event production was demonstrated. The tissue support for the liquid culture was two pieces of 100% acrylic felt covered by a single piece of filter paper.

TABLE 1

Data demonstrating the results of the wheat WDSDEs transformation liquid protocol used in a test. Successful transformation of wheat dry seed derived explants using a standard protocol.

| # of explants treated | # PCR-positive Events | % TF |
| --- | --- | --- |
| 4998 | 79 | 1.58 |

TABLE 2

A standard solid protocol using MS-based medium was used but with the culture media either autoclaved or filter sterilized. Successful transformation of wheat dry seed derived explants with different culture media preparation conditions.

| Culture media Preparation Conditions | # PCR positive Events | % TF |
| --- | --- | --- |
| Autoclaved | 10 | 0.20 |
| filter sterilized | 11 | 0.22 |

TABLE 3

A standard solid protocol using MS-based medium was used but with the modification that the two different strains of *Agrobacterium tumefaciens* were tested. Successful transformation of wheat dry seed derived explants (WDSDEs) using two different strains of *Agrobacterium tumefaciens* and two different bacterial preparation methods.

| Culture media preparation conditions | # PCR positive Events | % TF |
| --- | --- | --- |
| AB1 | 12 | 0.1% |
| AB32 | 36 | 0.4% |

TABLE 4

A standard solid protocol using MS-based medium was used but with the modification that the centrifugation was done either before or after the explants were inoculated with *Agrobacterium*. Successful transient transformation of wheat dry seed derived explants (WDSDEs) by inoculating the explants with *Agrobacterium tumefaciens* before or after explant centrifugation.

| | % WDSDEs expressing GUS |
| --- | --- |
| *Agrobacterium* then centrifugation | 78% |
| Centrifugation then *Agrobacterium* | 76% |
| *Agrobacterium* no centrifugation | 50% |

TABLE 5

A standard solid protocol using MS-based medium was used in this study but with the modification that several centrifugation speeds (gravitational forces) were tested. Successful transformation of wheat dry seed derived explants (WDSDEs) over a wide range of gravitational forces.

| Gravitational force (G) | # PCR positive Events | % TF |
| --- | --- | --- |
| 223 | 0 | 0 |
| 895 | 3 | 0.12 |
| 2013 | 1 | 0.04 |
| 3145 | 2 | 0.08 |

TABLE 6

A modified protocol using Modified MS-based medium with a gelled delay medium and liquid selection and regeneration media. The tissue support for the liquid media was two pieces of 100% acrylic felt covered by a single piece of filter paper. Pressure generated with a French press at the time of *Agrobacterium* inoculation. Successful transformation of wheat dry seed derived explants (WDSDEs) using pressure generated in a French press.

| Pressure (atm) | # TaqMan positive Events | % TF |
|---|---|---|
| 1 | 0 | 0.00 |
| 227 | 6 | 0.24 |
| 680 | 3 | 0.12 |

TABLE 7

A standard solid protocol using MS-based medium was used in this study but with the modification that several concentrations of 2,4-D were tested in the co-culture medium. In certain embodiments 5 mg/L 2,4-D was used. Successful transformation of wheat dry seed derived explants over a wide range of 2,4-D in the co-culture medium.

| 2,4-D concentration in co-culture medium (mg/L) | # PCR positive Events | % TF |
|---|---|---|
| 2 | 5 | 0.2 |
| 3 | 5 | 0.2 |
| 4 | 1 | 0.04 |
| 5 | 1 | 0.04 |

TABLE 8

A standard solid protocol using MS-based medium was used in this study but with the modification that light and dark co-culture conditions were tested. Successful transformation of wheat dry seed derived explants (WDSDEs) in either light or dark co-culture conditions.

| Co-culture Conditions | # PCR positive Events | % TF |
|---|---|---|
| Light | 2 | 0.04 |
| Dark | 6 | 0.12 |

TABLE 9

A standard solid protocol using MS-based medium was used in this study but with the modification that length of the co-culture time varied between treatments. Successful transformation of wheat dry seed derived explants (WDSDEs) over a range length of co-culture.

| Length of co-culture time (d) | # PCR positive Events | % TF |
|---|---|---|
| 2 | 1 | 0.02 |
| 3 | 3 | 0.19 |
| 4 | 1 | 0.06 |
| 5 | 1 | 0.06 |

TABLE 10

A standard solid protocol using MS-based medium was used in this study but with the modification that two levels of maltose were tested in the co-culture medium. Successful transformation of wheat dry seed derived explants with different carbohydrate levels in the co-culture medium.

| Maltose Concentration (g/l) | # PCR positive Events | % TF |
|---|---|---|
| 30 | 4 | 0.08 |
| 60 | 6 | 0.12 |

TABLE 11

A standard solid protocol using MS-based medium was used in this study but with the modification that several concentrations of Thidiazuron (TDZ) were tested in both the delay and selection media. Successful transformation of wheat dry seed derived explants over a wide range of Thidiazuron (TDZ) concentrations in delay and selection media.

| TDZ concentration (mg/L) | # PCR positive Events | % TF |
|---|---|---|
| 1 | 2 | 0.16 |
| 3 | 1 | 0.08 |
| 5 | 1 | 0.08 |
| 10 | 2 | 0.16 |

TABLE 12

A standard protocol using MS-based medium was used in this study but with the modification that the selection and regeneration media contained 30 µM glyphosate or 10 mg/l GENETICIN ® in the delay medium followed by 20 mg/l GENETICIN ® in the selection and regeneration media. Successful transformation of wheat dry seed derived explants both with antibiotic and herbicide selection of explants

| Selection agent | # PCR positive Events | % TF |
|---|---|---|
| GENETICIN ® | 2 | 0.02 |
| glyphosate | 6 | 0.12 |

TABLE 13

A standard protocol using MS-based medium was used in this study but with the modification that the selection medium was either liquid or gelled medium. The tissue support for the liquid culture was two pieces of 100% acrylic felt covered by a single piece of filter paper. Successful transformation of wheat dry seed derived explants with either liquid or gelled selection medium.

| Medium texture | # PCR positive Events | % TF |
|---|---|---|
| solid delay to liquid selection | 13 | 0.26 |
| solid delay to solid selection | 7 | 0.15 |

TABLE 14

A standard protocol using was used but with the modification either MS-based media (STL) or modified MS-based media (MID) was used in the process.

| Treatment | Starting # explants | # events to soil | # PCR Positive events | % TF |
|---|---|---|---|---|
| STL Media | 4366 | 43 | 43 | 0.98% |
| MID Media | 4810 | 81 | 80 | 1.66% |
| STL Media | 4284 | 32 | 32 | 0.75% |
| MID Media | 4998 | 80 | 79 | 1.58% |

Successful transformation of wheat dry seed derived explants (WDSDEs) using two different culture media series; STL=MS basal medium, MID=MS basal medium with elevated $NH_4NO_3$ and $K_2SO_4$.

TABLE 15

Successful inheritance of transgene after transformation of wheat dry seed derived explants. The standard protocol using MS-based medium was used to produce the R0 (T0) parental events to these R1 progeny.

| Transformation System | Wheat WDSDE N = 63 | |
|---|---|---|
| 1 and 1 or 2 Copy at R0 | Number of Events | % of Total Events |
| Intended Mendelian Segregation | 42 | 67% |
| Reduced Progeny Transmission | 13 | 21% |
| Multi Insertion Sites | 7 | 11% |

TABLE 16

Modified MS-based delay medium Recipe Number 4004 (liquid) or 3996 (gelled).

| Order of addition | Ingredients | Amount per liter | |
|---|---|---|---|
| 1 | MS Basal Salts, no Nitrogen (Phytotech M531) | 0.78 | g |
| 2 | Potassium Sulfate (Sigma P-8541) | 1.64 | g |
| 3 | Ammonium nitrate (Sigma A-7455) | 4.95 | g |
| 4 | MS Vitamins (100X -1208) | 10 | mL |
| 5 | Glutamine (Phytotech G229) | 0.5 | g |
| 6 | Casein Hydrolysate | 1 | g |
| 7 | Magnesium Chloride (Sigma M-0250) | 0.75 | g |
| 8 | MES (Sigma M-8250) | 1.95 | g |
| 9 | Maltose (Phytotech M588) | 60 | g |
| 10 | $CuSO_4 \cdot 5H_2O$ (1 mg/ml) | 1.25 | mL |
| 11 | Clearys | 0.03 | g |
| 12 | Bring to volume with TC water | | |
| 13 | pH to | 5.8 | |
| 14 | Agarose, Low EEO (Pisher BP1 | 3.5 | g |
| 15 | Autoclave. | | |
| 16 | Picloram (1 mg/ml) | 2 | mL |
| 17 | TDZ (1 mg/ml) | 3 | mL |
| 18 | Carbenicillin (40 mg/ml - 1196) | 10 | mL |
| 19 | Ticarcillin (100 mg/ml -1036) | 1 | mL |
| 20 | Cefotaxime (50 mg/ml -1686) | 4 | mL |

TABLE 17

Modified MS-based selection medium Recipe Number 3997.

| Order of addition | Ingredients | Amount per Liter | |
|---|---|---|---|
| 1 | MS Basal Salts, no Nitrogen (Phytotech M531) | 0.78 | g |
| 2 | Potassium Sulfate (Sigma P-8541) | 1.64 | g |
| 3 | Ammonium nitrate (Sigma A-7455) | 4.95 | g |
| 4 | MS Vitamins (100X -1208) | 10 | mL |
| 5 | Glutamine (Phytotech G229) | 0.5 | g |
| 6 | Casein Hydrolysate | 1 | g |
| 7 | Magnesium Chloride (Sigma M-0250) | 0.75 | g |
| 8 | MES (Sigma M-8250) | 1.95 | g |
| 9 | Maltose (Phytotech M588) | 30 | g |
| 10 | $CuSO_4 \cdot 5H_2O$ (1 mg/ml) | 1.25 | mL |
| 11 | Clearys | 0.03 | g |
| 12 | Bring to volume with TC water | | |
| 13 | pH to | 5.8 | |
| 14 | Autoclave. | | |
| 15 | Picloram (1 mg/ml) | 2 | mL |
| 17 | TDZ (1 mg/ml) | 3 | mL |
| 18 | Carbenicillin (40 mg/ml - 1196) | 10 | mL |
| 19 | Ticarcillin (100 mg/ml -1036) | 1 | mL |
| 20 | Cefotaxime (50 mg/ml -1686) | 4 | mL |
| 21 | Glyphosate (0.5M) | 0.05 | mL |

TABLE 18

Modified MS-based regeneration medium Recipe Number 3995.

| Order of addition | Ingredients | Amount per Liter | |
|---|---|---|---|
| 1 | MS Basal Salts (Phytotech M5 | 4.33 | g |
| 2 | MS Vitamins (100X -1208) | 10 | ml |
| 3 | Sucrose (Phytotech S391) | 30 | g |
| 4 | Proline (Sigma P-5607) | 0.69 | g |
| 5 | MES (Sigma M-8250) | 1 | g |
| 6 | Dissolve | | |
| 7 | Cleary's | 0.03 | g |
| 8 | Bring to volume with TC water | | |
| 9 | pH to | 5.8 | |
| 11 | Autoclave. | | |
| 12 | Carbenicillin (40 mg/ml - 1195) | 10 | ml |
| 13 | Cefotaxime (50 mg/ml -1686) | 4 | ml |
| 14 | Timentin (100 mg/ml - 1585) | 1 | ml |
| 15 | Glyphosate (0.5M - 1031) | 0.06 | ml |

TABLE 19

Rooting medium Recipe Number 3903.

| Order of addition | Ingredients | Amount per Liter | |
|---|---|---|---|
| 1 | MS Basal Salts | 4.33 | g |
| 2 | MMS Vitamins (500X) | 2 | mL |
| 3 | MES | 1.95 | g |
| 4 | Maltose | 40 | g |
| 5 | Cupric Sulfate (12.5 mg/ml) | 0.04 | mL |
| 6 | Cleary's | 0.03 | g |
| 7 | Bring to volume with TC water | | |
| 8 | pH with KOH to | 5.8 | |
| 9 | Gelzan CM | 3 | g |
| 10 | Autoclave. | | |
| 11 | Glyphosate (0.5M) | 0.06 | mL |
| 12 | Carbenicillin (250 mg/ml) | 1.6 | mL |
| 13 | Cefotaxime (100 mg/ml) | 2 | mL |
| 14 | Timentin (100 mg/ml) | 1 | mL |
| 15 | Ascorbic Acid (50 mg/ml) | 2 | mL |
| 16 | IBA (1 mg/ml) | 1 | mL |

TABLE 20

MS-based delay medium Recipe Number 3901.

| Order of addition | Ingredients | Amount per Liter | |
|---|---|---|---|
| 1 | MS Basal Salts | 4.33 | g |
| 2 | MS Vitamins (100X) | 10 | mL |
| 3 | Maltose | 60 | g |
| 4 | Glutamine | 0.5 | g |
| 5 | Casein Hydrolysate | 0.1 | g |
| 6 | Magnesium Chloride | 0.75 | g |
| 7 | MES | 1.95 | g |
| 8 | Clearys | 0.03 | g |
| 9 | Add TC water to bring to volume | | |
| 10 | pH to | 5.8 | |
| 11 | Agarose, Low EEO (Fisher BP1 | 3.5 | g |
| 12 | Filter sterilize with 0.22 micron unit* | 3.5 | g |
| 13 | Cupric Sulfate (12.5 mg/ml) | 0.1 | mL |
| 14 | Thidiazuron (1 mg/ml) | 3 | mL |
| 15 | Picloram (1 mg/mL) | 2 | mL |
| 16 | Carbenicillin (250 mg/ml) | 1.6 | mL |
| 17 | Cefotaxime (100 mg/ml) | 2 | mL |
| 18 | Timentin (100 mg/mL) | 1 | mL |

TABLE 21

MS-based selection medium Recipe Number 3902.

| Order of addition | Ingredients | Amount per Liter | |
|---|---|---|---|
| 1 | MS Basal Salts | 4.33 | g |
| 2 | MS Vitamins (100X) | 10 | mL |
| 3 | Maltose | 40 | g |
| 4 | Glutamine | 0.5 | g |
| 5 | Casein Hydrolysate | 0.1 | g |
| 6 | Magnesium Chloride | 0.75 | g |
| 7 | MES | 1.95 | g |
| 8 | Clearys | 0.03 | g |
| 9 | pH with KOH to | 5.8 | |
| 10 | Add TC water to bring to volume | | |
| 11 | Filter sterilize with 0.22 micron unit* | | |
| 12 | Cupric Sulfate (12.5 mg/ml) | 0.1 | mL |
| 13 | Thidiazuron (1 mg/ml) | 3 | mL |
| 14 | Picloram (1 mg/mL) | 2 | mL |
| 15 | Carbenicillin (250 mg/ml) | 1.6 | mL |
| 16 | Cefotaxime (100 mg/ml) | 2 | mL |
| 17 | Timentin (100 mg/mL) | 1 | mL |
| 18 | Glyphosate (0.5M) | 0.06 | mL |

TABLE 22

MS-based regeneration medium Recipe Number 3932.

| Order of addition | Ingredients | Amount per Liter | |
|---|---|---|---|
| 1 | MS Basal Salts | 4.33 | g |
| 2 | MMS Vitamins (500X) | 2 | mL |
| 3 | MES | 1.95 | g |
| 4 | Maltose | 40 | g |
| 5 | Cupric Sulfate (12.5 mg/ml) | 0.04 | g |
| 7 | Cleary's | 0.03 | g |
| 8 | Bring to volume with TC water | | |
| 9 | pH to | 5.8 | |
| 11 | Autoclave. | | |
| 12 | Glyphosate (0.5M) | 50 | ml |
| 13 | Carbenicillin (250 mg/ml) | 1.6 | ml |
| 14 | Cefotaxime (100 mg/ml) | 2 | ml |
| 15 | Timentin (100 mg/ml) | 1 | ml |

TABLE 23

MS-based co-culture medium Recipe Number 3091.

| Order of addition | Ingredients | Amount per Liter | |
|---|---|---|---|
| 1 | MS Basal Salts (Phytotech M524) | 0.433 | g |
| 2 | MS Vitamins (100X) | 10 | mL |
| 3 | Glutamine (Phytotech G229) | 0.5 | g |
| 4 | Casein Hydrolysate (Sigma C-9386) | 0.1 | g |
| 5 | Magnesium Chloride (Sigma M-0250) | 0.75 | g |
| 6 | MES (Sigma M-8250) | 1.95 | g |
| 7 | Maltose (Phytotech M588) | 40 | g |
| 8 | Ascorbic Acid (50 mg/ml) | 2 | ml |
| 9 | Bring to volume with TC water | | |
| 10 | pH w/KOH to | 5.8 | |
| 11 | Filter sterilize | | |

TABLE 24

MS-based delay medium Recipe Number 3892.

| Order of addition | Ingredients | Amount per Liter | |
|---|---|---|---|
| 1 | TC Water | 500 | ml |
| 2 | Agarose, Low EEO (Sigma A-6013) | 3.5 | g |
| 3 | Autoclave | | |
| 4 | Combine the following ingredients: | | |
| 5 | MS Basal Salts (Phytotech M524) | 4.33 | g |
| 6 | MS Vitamins (100x) | 10 | ml |
| 7 | Maltose (Phytotech M588) | 30 | g |
| 8 | Proline (Sigma P-5607) | 0.5 | g |
| 9 | Casein Hydrolysate (Sigma C-9386) | 1 | g |
| 10 | Thiamine HCL (0.5 mg/mL) | 2 | ml |
| 11 | Cupric Sulfate (12.5 mg/mL) | 0.1 | ml |
| 12 | Bring to volume with TC water | 500 | ml |
| 13 | pH w/KOH to | 5.8 | |
| 14 | Filter Sterilize | | |
| 15 | Add to Autoclaved Agarose mixture | | |
| 16 | Add the following filter sterilized ingredients: | | |
| 17 | Picloram (1 mg/mL) | 2 | ml |
| 18 | Thidiazuron (1 mg/mL) | 3 | ml |
| 19 | Carbenicillin (250 mg/mL) | 1.6 | ml |
| 20 | Cefotaxime (100 mg/mL) | 2 | ml |
| 21 | Timentin (100 mg/mL) | 1 | ml |

Example 10

Basal Respiration Rate of Wheat WDSDEs and Pre-Cultured Immature Embryos (PCIEs) Prior to Transformation Typical wheat transformation is associated with some kind of actively growing callus tissue such as that derived from immature embryos (PCIEs). It has in particular been believed to date that rapidly dividing, i.e. metabolizing cells, are needed for efficient *A. tumefaciens*-mediated transformation. Since metabolic activity of a cell depends on the availability of ATP and mitochondrial activity is the primary source of ATP in non-photosynthesizing tissues, measuring the oxygen consumption (respiration rate) of a tissue can give a fair assessment of the metabolic activity of the tissue if it is demonstrated that the oxygen consumption is via the terminal oxidase of the mitochondrial electron transport chain. An analysis was therefore carried out on wheat WDSDEs of oxygen consumption as an indicator of metabolic rate.

Figure 5:
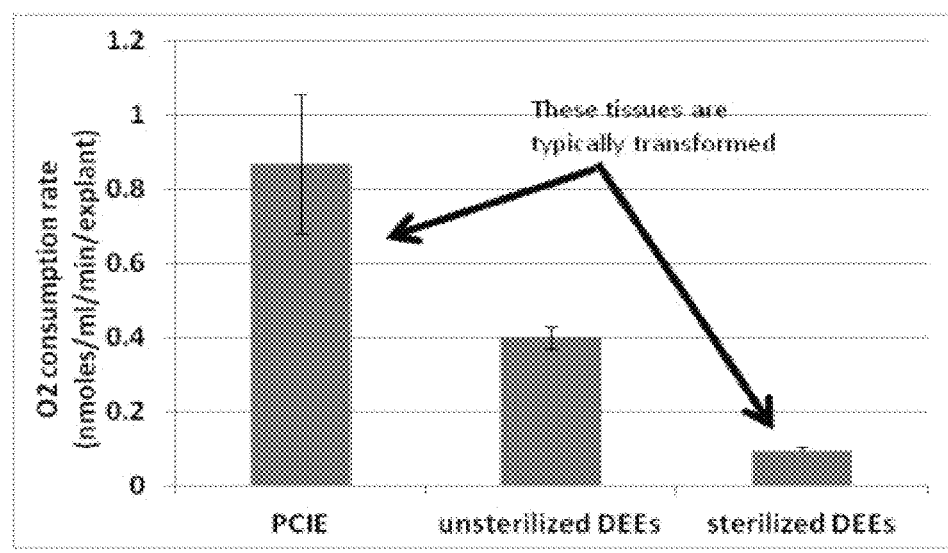
FIG. 5: Shows oxygen consumption rates of wheat tissues typically transformed.

As shown in FIG. 5, WDSDEs facilitate transforming wheat tissue that is in a state of minimal mitochondrial activity as compared to callus. It was found that transformation under these respiratory conditions gives sufficient metabolic activity for plasmid DNA integration into the plant genome, while surprisingly minimizing the tissue response to attack by *A. tumefaciens*. The end result is an easily obtained, stored and transformed wheat explant, therefore representing a significant advance over the art.

Example 11

Wheat WDSDE Respiration and Transformation

A study was carried out on the respiration rate of WDS-DEs during transformation and in relation to different experimental parameters. Sterilized wheat WDSDEs were inoculated in 50 ml CORNING® conical centrifuge tubes with 35 ml of *Agrobacterium* strain AB32 at an O.D.660 of 0.3-0.5 for 30 minutes while being centrifuged at 800-1000 g in a swing bucket BECKMAN COULTER® ALLEGRA® 6 centrifuge. A level 1/16th teaspoon of WDSDEs was added to a co-culture plate containing a single WHATMAN® #1 filter paper and 1.25 ml of 3091 medium plus 5 mg/L 2,4-D. The WDSDEs were evenly distributed across the filter paper with a spatula. The co-culture plates were incubated in the dark at 23° C. and 70% relative humidity. If the transformation was carried through to completion delay, selection, and regeneration all took place at 25° C., 16 hour photoperiod and 50-220 DE from Sylvania Pentron™ 4100 K 14W fluorescent bulbs.

To examine imbibition, sterilized CA905-752 WDSDEs were placed in 5 ml of sterile water in a Petri dish. At different time points 50 WDSDEs were collected into pre-tarred Petri dishes, excess water blotted away and the WDSDEs weighed. To address cell membrane integrity, the conductivity of 10 ml sterile water containing 100 WDSDEs was measured over the course of six hours.

Oxygen Consumption:

A small amount of sterilized CA905-752 WDSDEs (1/16th teaspoon) was immediately placed in a Petri dish on filter paper wetted with 1.25 ml 3091 medium. The WDSDEs were spread over the co-culture plate with a spatula and co-cultured in the dark at 23° C. with a 70% relative humidity. At various time points during co-culture, 50 WDSDEs were collected, placed in a nylon sling and suspended in 2.5 ml of water in a 25° C. water-cooled chamber containing a Clark oxygen electrode. Oxygen consumption was measured for 10-15 minutes. Other treatments included measuring oxygen consumption of WDSDEs inoculated with *A. tumefaciens* and measuring the oxygen consumption of the bacteria.

Respiration Determination:

Oxygen consumption was measured for 10-15 minutes as previously described but about half way through a measurement, either 4 mM KCN (made in 0.5 M potassium phosphate buffer) or 4 mM salicylhydroxamic acid (SHAM, made in 0.25 M potassium phosphate buffer) was added to the chamber. Other treatments included soaking aliquots of 50 WDSDEs for 30-50 minutes in either 4 mM KCN or 4 mM SHAM prior to measuring oxygen consumption.

Results:

Imbibition of wheat WDSDEs was rapid, taking 30 minutes to sterilize and float 300 WDSDEs and that was sufficient time for the WDSDEs to totally imbibe water. If there was no 2,4-D in the co-culture medium a wheat WDSDE began to germinate. By day two on co-culture medium (1.25 ml 3091 medium) most WDSDEs were showing radical emergence with 2-3 mm long roots by day three. The co-culture medium cannot sustain wheat seedling growth, however. When WDSDEs were exposed to the co-culture medium for up to six days, growth essentially stopped.

Figure 6:
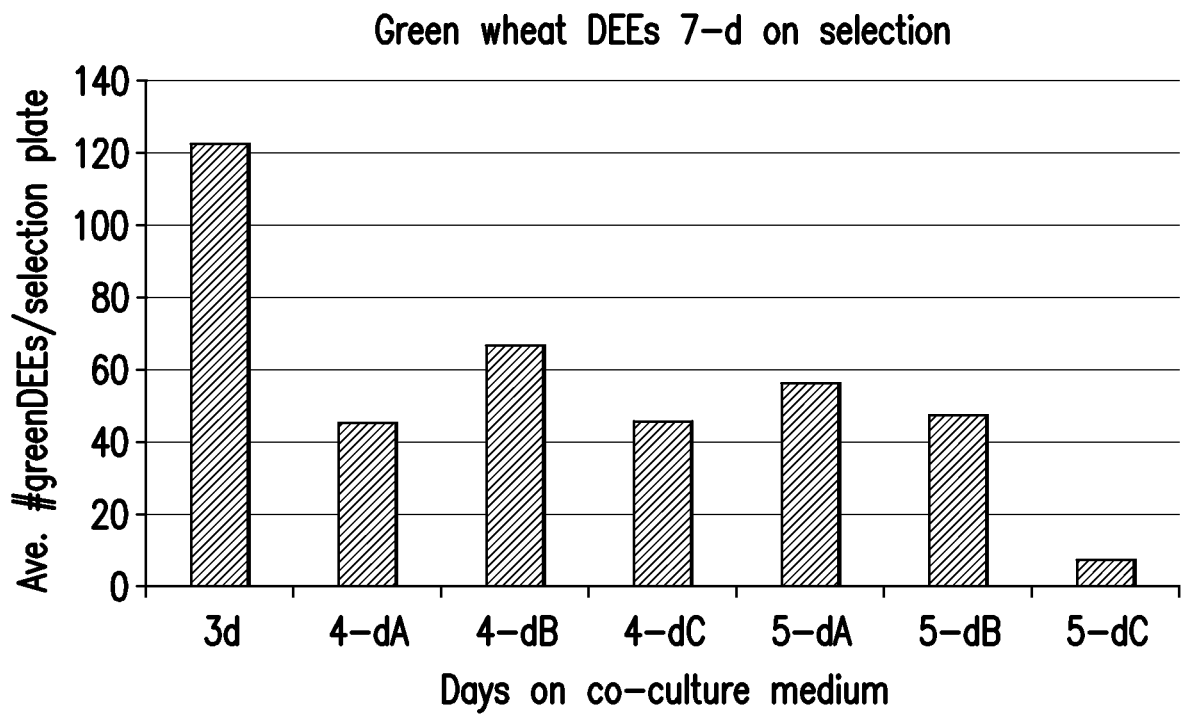
FIG. 6: Shows the number of green WDSDEs present on 25 mg/L selection plates (3892 medium) 7-d after co-culture. The days with letters indicate individual co-culture plates formed those selection plates.
Figure 7:
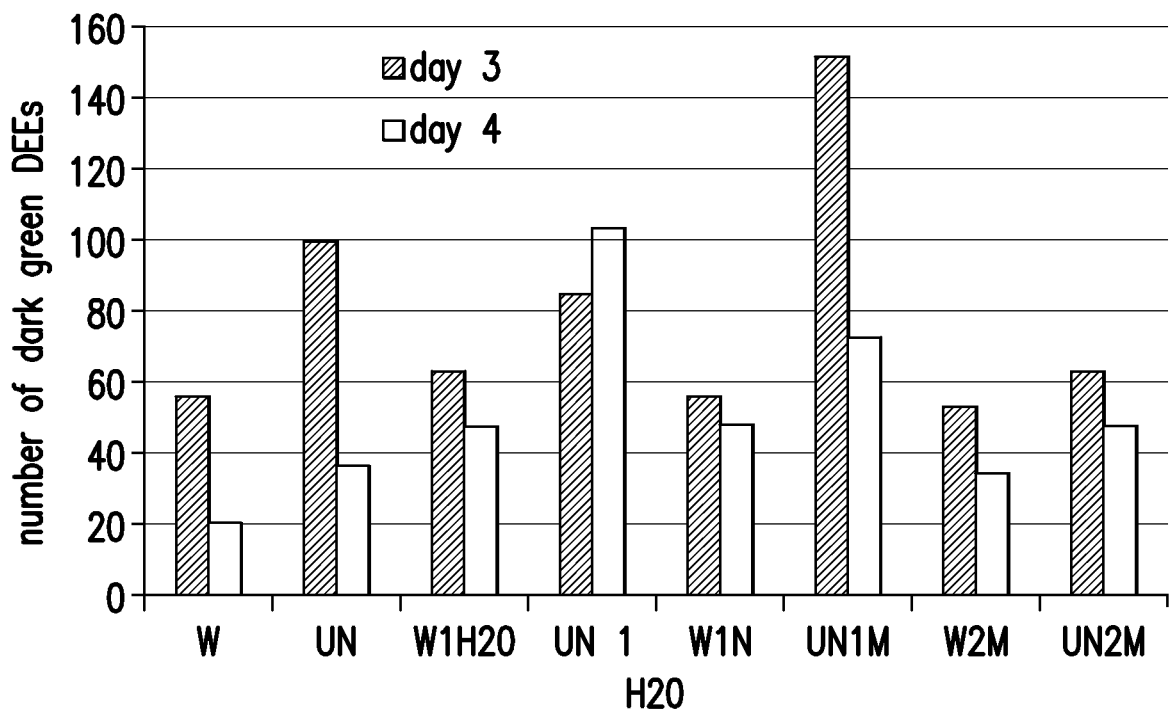
FIG. 7: Shows the number of green WDSDEs present on 25 mg/L selection plates (3892 medium) 7-d after co-culture.

Length of Co-Culture:

Considering that WDSDE co-culture with *Agrobacterium* was typically 4-5 days it was investigated whether this time was too long for the health of the WDSDE. Two studies were set up to look at WDSDE survival as measured by the presence of green WDSDEs on selection medium seven days post-co-culture. A number of different treatments were being tested in these experiments but in all of them the WDSDEs were co-cultured 3, 4 and sometimes 5 days before being moved to a delay medium (Recipe Number 3892) containing 25 mg/L geneticin. From these two studies there was a consistent trend that the longer a treatment was in co-culture the fewer green WDSDEs (interpreted as healthy surviving WDSDEs) were present 7-d after the co-culture (FIGS. 6 and 7).

Transgene Expression:

The long co-culture time for wheat WDSDEs had been typically determined by when transient GFP or GUS expression was seen. In general the earliest that transient GUS expression was detected in CA905-752 WDSDEs moved from co-culture plates was three days with very slight if any expression at two days. Considering that both GUS and GFP are proteins, transient expression will depend not only on the amount of transformation that occurred but also on the amount of protein produced by the time of the assay. Consequently, a very successful transformation might have occurred but be undetected if not enough time passed for enough protein to accumulate by the time of the assay. To examine this accumulation phenomena; 10,000 WDSDEs were transformed and co-cultured for 2-3 days. After two days in co-culture half the WDSDEs were moved to 3892 delay medium containing no selection agent and two 50-embryo samples were collected for GUS analysis. After three days in co-culture the rest of the WDSDEs were moved to 3892 delay medium and two 50-embryo samples were collected for GUS analysis. In addition, two 50 embryo samples were collected for GUS analysis from the delay plates created from the two day co-cultured WDSDEs. These later embryos were chronologically the same age as the WDSDEs from the three day co-culture but were only exposed to co-culture conditions for two days.

Figure 8:
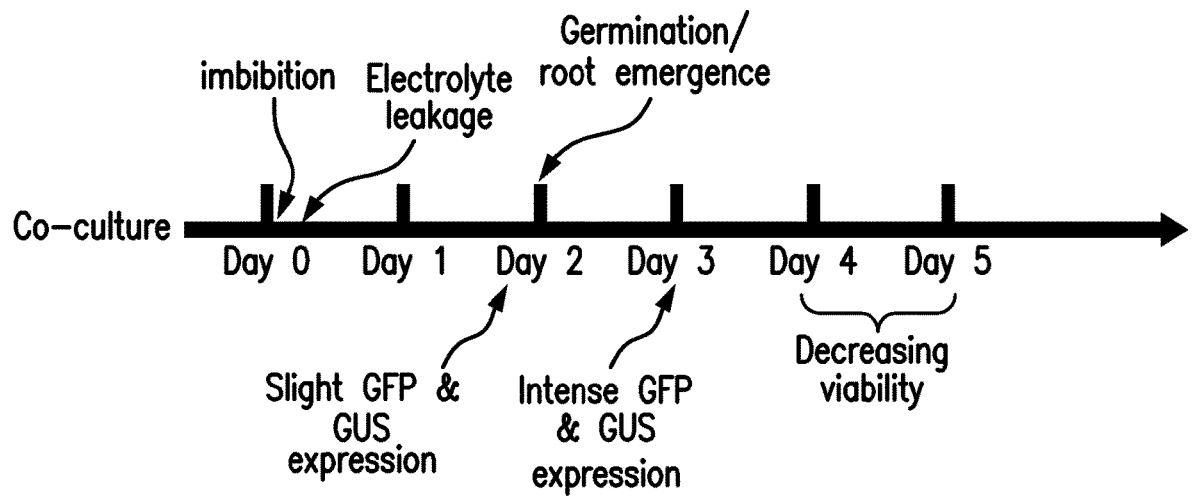
FIG. 8: Shows a summary of WDSDEs response during sterilization and co-culture.

As previously noted, GUS expression of WDSDEs moved from co-culture at day two was almost nonexistent with only 10% percent of the WDSDEs expressing GUS (FIG. 8). Around 85% of the WDSDEs moved from co-culture on day two expressed GUS after one day on delay medium. This was a similar percentage as WDSDEs left on co-culture medium for three days and similar to other treatments in this same experiment left on co-culture for three days. These results suggest that the long co-culture typically used in wheat WDSDE transformations may not be necessary as long as selection is not immediately used after co-culture.

Figure 9:
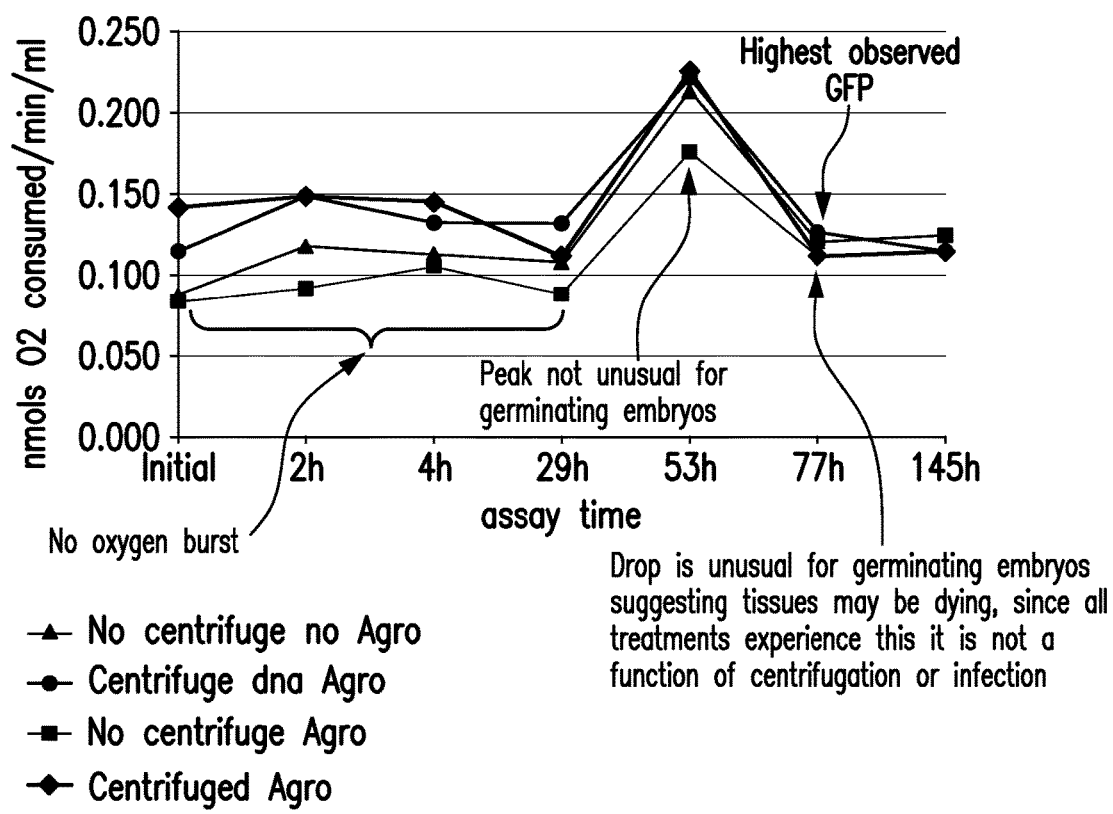
FIG. 9: Shows the oxygen consumption of WDSDEs after inoculation with *A. tumefaciens*.

Oxygen Consumption:

When WDSDEs were inoculated with *A. tumefaciens* and oxygen consumption was measured, an oxygen burst was not detected at the time points examined and the oxygen consumption varied little when compared to non-inoculated and non-centrifuged treatments (FIG. 9). The initial oxygen consumption of a population of 50 WDSDEs was measured at 0.08-1.4 nmoles $O_2$. This oxygen consumption then increased with a peak at about day two of co-culture.

Figure 10:
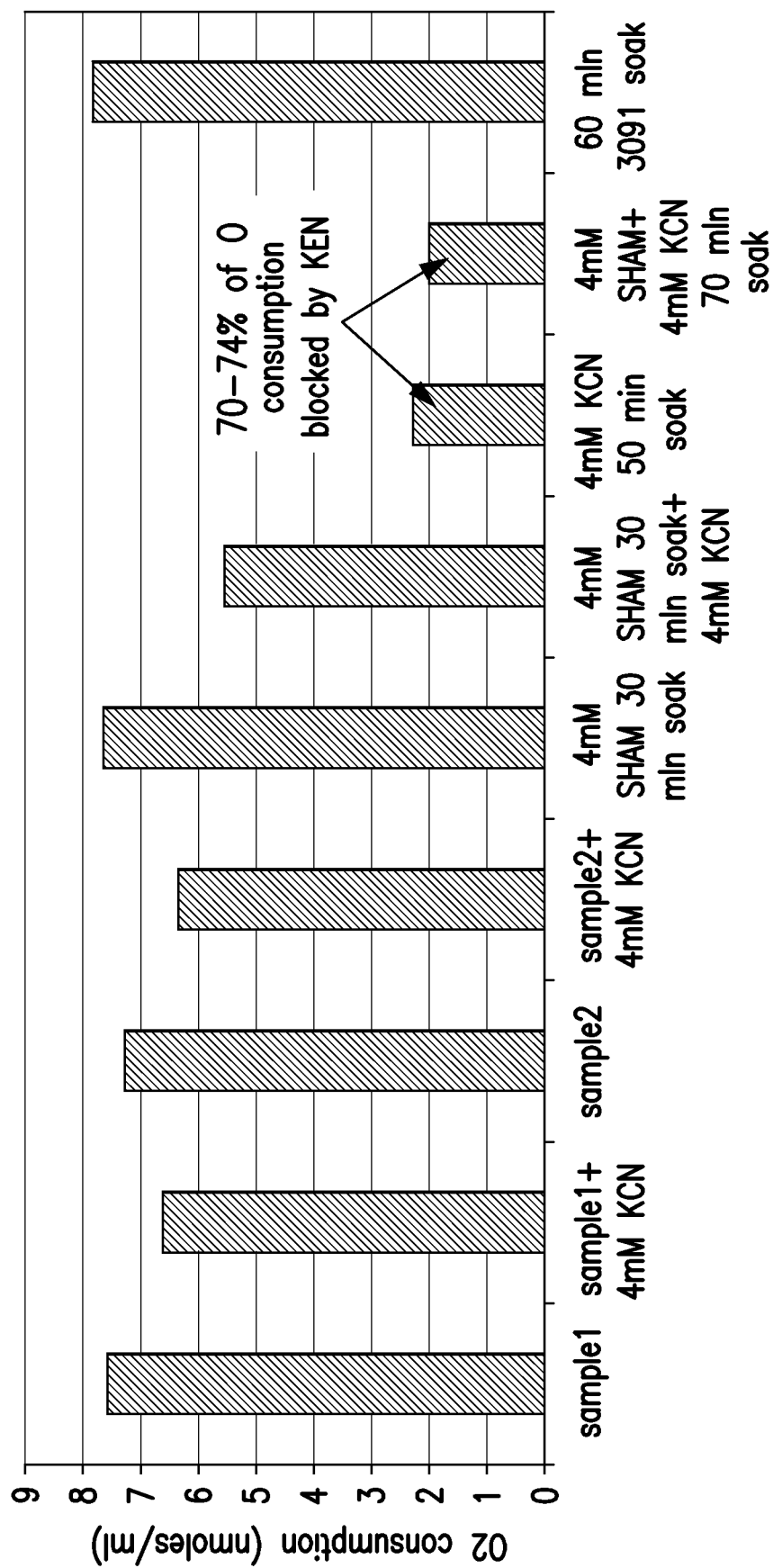
FIG. 10: Shows the effect of respiration inhibitors on oxygen consumption by wheat WDSDEs after three days in co-culture.

Cyanide and antimycin are often used to inhibit the terminal cytochrome oxidase of mitochondrial respiration, while salicyhydroxamic acid (SHAM) and n-propyl gallate are used to block the alternative respiration oxidase. To determine what consumes oxygen in wheat WDSDEs both cyanide and SHAM were tested. Very little effect was seen when KCN or SHAM was added to the reaction chamber during an oxygen measurement (FIG. 10). This may be expected since time is required for the compounds to diffuse into the tissue and reach sites to inhibit. When the WDSDEs were soaked in KCN, 70-74% of the oxygen consumption seen in the control treatments was suppressed suggesting that all but about 30% of the oxygen consumption by wheat WDSDEs seen in previous experiments was due to mitochondrial respiration. No effect was seen with soaking WDSDEs in SHAM suggesting that alternative oxidation does not function in the early stages of WDSDE germination.

A similar study was conducted with *A. tumefaciens* inoculated wheat WDSDEs but with a 3700 g centrifugation for 15 minutes and oxygen consumption was measured with the addition of soaking some WDSDEs in 4 mM KCN. The oxygen consumption was only measured on day 1 and 3. After 3 days in co-culture, the centrifuged WDSDEs that were not inoculated maintained the portion of oxygen consumption that was cyanide sensitive more so than did the non-centrifuged, uninoculated WDSDEs. The cyanide sensitive oxygen consumption of inoculated wheat WDSDEs plummeted to just 2% of the level measured on day 1. A similar drop in cyanide sensitive oxygen consumption was seen with WDSDEs left in co-culture for 5 days. These 5 day old WDSDEs had stopped growing and were beginning to turn brown, so this drop in cyanide sensitive oxygen consumption might be an indication of stressed tissue. The lack of cyanide sensitive oxygen consumption indicates that normal mitochondrial respiration was compromised and oxygen was being consumed by other means such as the alternative oxidation pathway or the generation of reactive oxygen products such as peroxide. These results indicate that wheat WDSDEs may mount a very strong stress response to *A. tumefaciens* infection and prolonged co-culture.

To ensure that the results were not measuring *A. tumefaciens* oxygen consumption rather than that of wheat WDSDEs, or a mixture, the oxygen consumption of *A. tumefaciens* alone was measured with and without cyanide present. In addition, the oxygen consumption of inoculated wheat WDSDEs with and without cyanide and the reaction vessel solution with WDSDEs removed was assayed. When the oxygen consumption of inoculated wheat WDSDEs was measured and then the WDSDEs were removed from the reaction vessel, little to no oxygen consumption could be detected in the solution from which the WDSDEs were removed suggesting that very little *A. tumefaciens* was contributing to the measured oxygen consumption when the WDSDEs were present.

The observations indicated that although *A. tumefaciens* is present during an oxygen consumption measurement of inoculated wheat WDSDEs, the pattern of oxygen consumption by the inoculated WDSDEs does not match that of *A. tumefaciens*. This all supports the idea that what has been measured has been primarily mitochondrial oxygen consumption by wheat WDSDEs and that the bacteria interfere little with these measurements.

Conclusion:

The studies showed that wheat WDSDE imbibition is rapid, occurring within the normal time of WDSDE sterilization and floatation. In the co-culture plate oxygen consumption by wheat WDSDEs begins at a range of about 0.08-1.4 nmoles $O_2$/ml of water/50 WDSDEs, increases for one to two days and then decreases during the remainder of the co-culture. This decrease is partially due to the presence of 5 mg/L 2,4-D in the co-culture plate. In WDSDEs not exposed to 2,4-D, the observations are similar, but the decline is slightly delayed and the increase in oxygen consumption is greater. If WDSDEs are co-cultured on 50 ml of CM4C medium there is no decline in oxygen consumption and the WDSDEs proceed to expand radicals and coleoptiles suggesting that the decline in oxygen consumption is partially due to nutrient and water deficiency with prolonged co-culture. The oxygen consumption is mostly cyanide sensitive, most likely due to mitochondrial respiration. With prolonged exposure to co-culture conditions, fewer and fewer WDSDEs survive in the delay culture step as indicated by greening after 7 days on delay medium. A shorter co-culture exposure yields more surviving WDSDEs with comparable transient GUS activity.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

What is claimed is:

1. A method of producing a transgenic wheat plant comprising selecting a dry viable wheat dry seed derived explant for an oxygen consumption rate of from about 0.05 to about 0.5 nMoles $O_2$/ml/min/explant; transforming the explant with an *Agrobacterium* comprising a heterologous DNA, wherein the explant is competent for genetic transformation and comprises an intact embryo including the scutellum and embryonic axis; wherein the endosperm and pericarp of the dry wheat seed have been substantially removed from the explant; wherein the seed from which the dry viable wheat dry seed derived explant is prepared comprises a moisture content of about 4% to about 13.5%;

co-culturing said explant in the presence of the *Agrobacterium*; culturing said explant in the presence of plant growth regulators to produce multiple buds following said transforming and co-culturing steps; and regenerating the transgenic wheat plant from the explant with multiple buds, wherein the selected explant has an increased probability of survival following transformation compared to an explant which does not have said oxygen consumption rate.

2. The method of claim 1, wherein the heterologous DNA comprises a selectable marker.

3. The method of claim 2, wherein the selectable marker confers tolerance to a selective agent selected from the group consisting of glyphosate, streptomycin, bialaphos, glufosinate, paromomycin, geneticin, and kanamycin.

4. The method of claim 1, comprising culturing the explant for from about 0 hours to about 112 days prior to said transforming.

5. The method of claim 1, comprising transforming the explant within about 2 hours of first contacting the explant with an aqueous solution.

6. The method of claim 1, wherein transforming said explant is carried out without generating a callus from the explant prior to transformation.

7. The method of claim 1, wherein the transgenic wheat plant is produced without generating a callus from said explants prior to transformation.

8. The method of claim 1, comprising decontaminating the explant prior to transforming the explant.

9. The method of claim 1, comprising storing the explant for from about 1 hour to about 2 years prior to said transforming.

10. The method of claim 1, comprising transforming a plurality of explants according to claim 1.

11. The method of claim 1, wherein the explant comprises an internal moisture content at which the explant does not germinate without addition of hydration.

12. The method of claim 1, wherein the explant is stored at an internal moisture content of from about 5% to about 12% prior to rehydration of the explant prior to or concurrently with said transforming.

13. The method of claim 1, further comprising obtaining transgenic progeny from the transgenic wheat plant regenerated from the explant, wherein the progeny comprise the heterologous DNA.

14. The method of claim 1, wherein the explant is from about 0.75 mm$^2$ to about 2 mm$^2$ in size.

15. The method of claim 1, wherein said transforming comprises co-culturing the explant with *Agrobacterium* for not more than about 3 days.

16. A method of producing a transgenic progeny wheat plant comprising obtaining a transgenic wheat plant prepared by the method of claim 1; and obtaining transgenic progeny of the transgenic wheat plant that comprise the heterologous DNA.

* * * * *